(12) United States Patent
Roelvink et al.

(10) Patent No.: US 8,283,461 B2
(45) Date of Patent: Oct. 9, 2012

(54) MULTIPLE PROMOTER EXPRESSION CASSETTES FOR SIMULTANEOUS DELIVERY OF RNAI AGENTS

(75) Inventors: Petrus W. Roelvink, Campbell, CA (US); David A. Suhy, San Ramon, CA (US); Alexander A. Kolykhalov, Mountain View, CA (US)

(73) Assignee: Benitec, Inc., Melbourne (AU)

( * ) Notice: Subject to any disclaimer, the term of this patent is extended or adjusted under 35 U.S.C. 154(b) by 396 days.

(21) Appl. No.: 12/723,466

(22) Filed: Mar. 12, 2010

(65) Prior Publication Data
US 2011/0003378 A1 Jan. 6, 2011

Related U.S. Application Data

(62) Division of application No. 11/072,592, filed on Mar. 4, 2005, now Pat. No. 7,727,970.

(60) Provisional application No. 60/553,920, filed on Mar. 17, 2004, provisional application No. 60/550,504, filed on Mar. 5, 2004.

(51) Int. Cl.
C07H 21/04 (2006.01)
C12N 15/00 (2006.01)
A61K 48/00 (2006.01)

(52) U.S. Cl. ............... 536/24.5; 435/320.1; 514/44 R

(58) Field of Classification Search ............... 536/24.5; 514/44 R; 435/320.1
See application file for complete search history.

(56) References Cited

U.S. PATENT DOCUMENTS

| 5,585,258 | A | 12/1996 | Houghton et al. |
| 6,127,116 | A | 10/2000 | Rice et al. |
| 6,218,181 | B1 | 4/2001 | Verma et al. |
| 6,472,180 | B1 | 10/2002 | Houghton et al. |
| 6,509,323 | B1 | 1/2003 | Davis et al. |
| 7,727,970 | B2 | 6/2010 | Roelvink et al. |
| 2002/0162126 | A1 | 10/2002 | Beach et al. |
| 2004/0053876 | A1 | 3/2004 | Turner et al. |
| 2004/0214329 | A1 | 10/2004 | Kay et al. |

FOREIGN PATENT DOCUMENTS

| CA | 2 468 955 | 6/2003 |
| CA | 2 479 409 | 9/2003 |
| CN | 1611606 | 5/2005 |
| WO | WO 99/49029 | 9/1999 |
| WO | WO 01/83736 | 11/2001 |
| WO | WO 03/016572 | 2/2003 |
| WO | WO 03/022052 | 3/2003 |
| WO | WO 03/070750 | 8/2003 |
| WO | WO 03/078629 | 9/2003 |
| WO | WO 03/079757 | 10/2003 |
| WO | WO 2004/011647 | 2/2004 |

OTHER PUBLICATIONS

In the U. S. Patent and Trademark Office, Non-Final Office Action in re: U.S. Appl. No. 11/072,592, dated Mar. 3, 2008, 7 pages.
In the U. S. Patent and Trademark Office, Non-Final Office Action in re: U.S. Appl. No. 11/072,592, dated Dec. 11, 2008, 8 pages.
International Search Report for PCT/US2005/007447 dated Jan. 3, 2006.
Blight et al., "Efficient Initiation of HCA RNA Replication in Cell Culture," *Science*, 2000; 290:1972-1974.
Boden et al., "Human Immunodeficiency Virus Type 1 Escape from RNA Interference," *J Virol.*, 2003; 77(21):11531-11535.
Boden, et al., "Promotor Choice Affects the Potency of HIV-1 Specific RNA Interference," *Nucl. Acids Res.*, 2003; 31(17):5033-5038.
Cavazzana-Calvo et al., "Gene Therapy of Human Severe Combined Immunodeficiency (SCID)-X1 Disease," *Science*, 2000; 288:669-672.
Chen et al.,"Minicircle DNA Vectors Devoid of Bacterial DNA Result in Persistent and High-Level Transgene Expression in Vivo," *Molecular Therapy*, 2003; 8(3):495-500.
Domitrovich et al., "Multiple, Dispersed Human U6 Small Nuclear RNA Genes with Varied Transcriptional Efficiencies," *Nucl. Acids Res.*, 2003; 31(9):2344-2352.
Elbashir et al., "Duplexes of 21-Nucleotide RNAs Mediate RNA Interface in Cultured Mammlian Cells," *Nature*, 2001; 411:494-498.
Elbashir et al., "Functional Anatomy of siRNAs for Mediating Efficient RNAi in Drosophila Melanogaster Embryo Lysate," *EMBO. J.*, 2001; 20(23):6877-6888.
Fire et al., Potent and Specific Genetic Interference by Double-Stranded RNA in *Caenorhaditis elegans*, *Letters to Nature*, 1998; 391: 806-811.
Fu et al., "Self-Complementary Adeno-Associated Virus Serotype 2 Vector: Global Distribution and Broad Dispersion of AAV-Mediated Transgene Expression in Mouse Brian," *Molec. Therapy*, 2003; 8(6):911-917.
Furth et al., "Gene Transfer into Somatic Tissues by Jet Injection," *Anal Biochem.*, 1992; 205(2):365-368.
Gitlin et al.,"Short Interfering RNA Confers Intracellular Antiviral Immunity in Human Cells," *Nature*, 2002; 418:430-434.
Gitlin et al., "Poliovirus Escape From RNA Interference: Short Interfering RNA-Target Recognition and Implications for Therapeutic Approaches," *Journal of Virology*, 2005; 79(2):1027-1035.
Grimm et al., "Preclinical In Vivo Evaluation of Pseudotyped Adeno-Associated Virus Vectors for Liver Gene Therapy," *Blood*, 2003; 102(7):2412-2419.
Guidotti et al., "Noncytolytic Control of Viral Infections by the Innate and Adaptive Immune Response," *Annu. Rev. Immunol*, 2001; 19:65-91.
Harborth et al., "Sequence Chemical, and Structural Variation of Small Interfering RNAs and Short Hairpin RNAs and the Effect on Mammalian Gene Silencing," *Antisense Nucleic Acid Drug Dev.*, 2003; 13(2):83-105.
Higashibata et al., "Identification of Promoter Regions Involved in Cell-and-Developmental Stage-Specific Osteopontin Expression in Bone, Kidney, Placenta, and Mammary Gland: an Analysis of Transgenic Mice," *J Bone Miner Res.*, 2004; 19(1):78-88.

(Continued)

Primary Examiner — J. E. Angell
(74) Attorney, Agent, or Firm — Patton Boggs LLP

(57) ABSTRACT

The present invention provides multiple-promoter expression cassettes for simultaneous delivery of RNAi, preferably to mammalian cells in vivo.

10 Claims, 24 Drawing Sheets

OTHER PUBLICATIONS

Hoggatt et al., "Cell-Specific Regulatory Modules Control Expression of Genes in Vascular and Visceral Smooth Muscle Tissues," *Circ. Res.*, 2002; 91(12):1151-1159.

Karlin et al., "Applications and Statistics for Multiple High-Scoring Segments in Molecular Sequences", *Proceedings of the National Academy of Science*, 1993; 90:5873-5877.

Kawasaki, et al. "Short Hairpin Type of dsRNAs that are Controlled by tRNA$^{Val}$ Promoter Significantly Induce RNAi-Mediated Gene Silencing in the Cytoplasm of Human Cells," *Nucleic Acids Res.*, 2003; 31(2):700-707.

Kay et al., "Looking into the Safety of AAV Vectors," *Nature*, 2003; 424: 251.

Klein, et al. "Inhibition of Hepatitis B Virus Replication In Vivo by Nucleoside Analogues and siRNA," *Gastroenterology*, 2003; 125(1):9-18.

Kurreck, J. "Antisense Technologies Improvement Through Novel Chemical Modifications," *Eur. J. Bioch.*, 2003; 20:1628-1644.

Maraia et al., "Gene Encoding Human Ro-Associated Autoantigen Y5 RNA," *Nucleic Acids Res.*, 1994; 24(18):3552-3559.

Maraia et al., "The Human Y4 Small Cyptoplasmic RNA gene is controlled by Upstream Elements and Resides on Chromosome 7 With All Other hY scRNA Genes," *Nucleic Acids Res.*, 1994; 22(15): 3045-3052.

Mccaffrey et al., "Inhibition of Hepatitis B Virus in Mice by RNA Interface." *Nature Biotech.*, 2003; 21(6):639-644.

McCaffrey et al., "RNA Interface in Adult Mice," *Nature*, 2002; 418:38-39.

McCarty et al., "Self-Complementary Recombinant Adeno-Associated Virus (scAAV) Vectors Promote Efficient Transduction Independently of DNA Synthesis," *Gene Therapy*, 2001; 8:1248-1254.

Miller, et al. "Allele-Specific Silencing of Dominant Disease Genes," *PNAS*, 2003, 100(2):7195-7200.

Mingozzi et al., "Improved Hepatic Gene Transfer by Using an Adeno-Associated Virus Serotype 5 Vector," *J. Virol.*, 2002; 76(20):10497-10502.

Muzyczka, "Use of Adeno-Associated Virus as a General Transduction Vector for Mammalian Cells," *Current Topics in Microbiology Immunology*, 1992; 158:97-129.

Myers et al., "Optimal Alignments in Linear Space," *Computer Applications in the Biosciences*, 1988; 4(1):11-17.

Nakai et al., "A Limited Number of Transducible Hepatocytes Restricts a Wide-Range Linear Vector Dose Response in Recombinant Adeno-Associated Virus-Mediated Liver Transduction," *J Virol.*, 2002; 76(22):11343-11349.

Pearson et al., "Improved Tools for Biological Sequence Comparison," *Proceedings of the National Academy of Science of the United States of America*, 1988; 85: 2444-2448.

Perri et al., "Replicon Vectors Derived from Sindbis Virus and Semliki Forest Virus that Establish Persistent Replication in Host Cells," *J Virol.*, 2002; 74(20):9802-9807.

Sohal et al., "Temporally Regulated and Tissue-Specific Gene Manipulations in the Adult and Embryonic Heart Using a Tamoxifen-Inducible Cre Protein," *Circ. Res.*, 2001; 89(1):20-25.

Shlomai et al., "Inhibition of Hepatitis B Virus Expression and Replication by RNA Interference," *Hepatology*, 2003; 37(4):764-770.

Tang et al., "Genetic Immunization is a Simple Method for Eliciting and Immune Response," *Nature*, 1992; 356:152-154.

Thomas et al., "Progress and Problems with the Use of Viral Vectors for Gene Therapy", *Nature Reviews*, 2003; 4:346-358.

Thomas et al., "Rapid Uncoating of Vector Genomes is the Key to Efficient Liver Transduction with Pseudotyped Adeno-Associated Virus Vectors," *J. Virol.*, 2004; 78(6):3110-3122.

Tomar et al., "Use of Adeno-Associated Viral Vector for Delivery of Small Interfering RNA," *Oncogene*, 2003; 22: 5712-5715.

Tuschl et al., "Targeted mRNA Degradation by Double-Stranded RNA In Vitro", *Genes & Dev.*, 1999; 13:3191-3197.

Xia et al., "An Enhanced U6 Promoter for Synthesis of Short Hairpin RNA," *Nucleic Acids Res.*, 2003; 31(17):e100.

Yant et al., "Transposition from a Gutless Adeno-Transposon Vector Stabilizes Transgene Expression in Vivo," *Nature Biotech.*, 2002; 20:999-1004.

Yant et al., "Somatic Integration and Long-Term Transgene Expression in Normal and Haemophilic Mice using a DNA Transposon System," *Nature Genetics*, 2000, 25:35-41.

Yin Y et al.., "The Potential Medical Application of RNAi Technology," *Foreign Medical Science: Section of Molecule Biology*, 2003; 25(6):378-381. With English-language Abstract.

Ying et al., "Selective Inhibition of Hepatitis B Virus Replication by RNA Interference", *Biochem. Biophys. Res. Commun.*, 2003; 309(2):482-484.

Yokota et al., "Inhibition of Intracellular Hepatitis C Virus Replication by Synthetic and Vector-Derived Small Interfering RNA's," *EMBO Reports*, 2003; 4(6):602-608.

Zhang et al., "Multiple Variable First Exons: A Mechanism for Cell- and Tissue-Specific Gene Regulation," *Genome Res.*, 2004; 14(1):79-89.

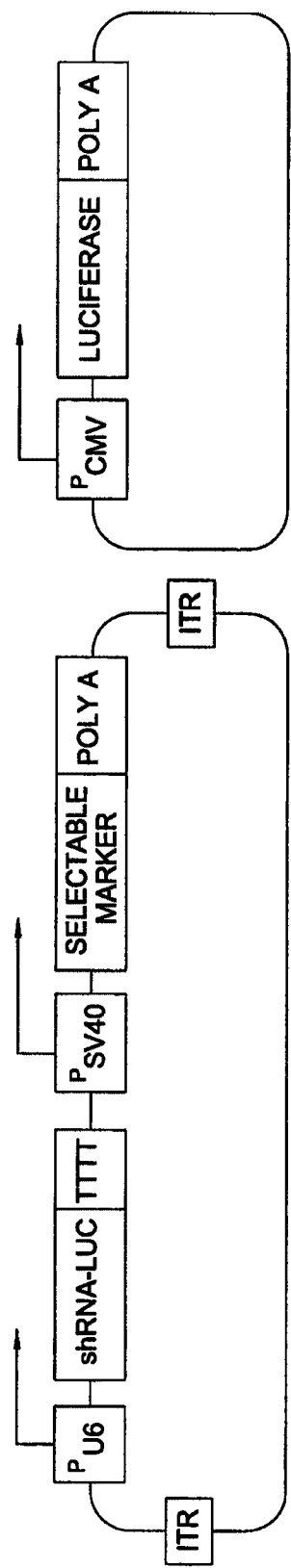
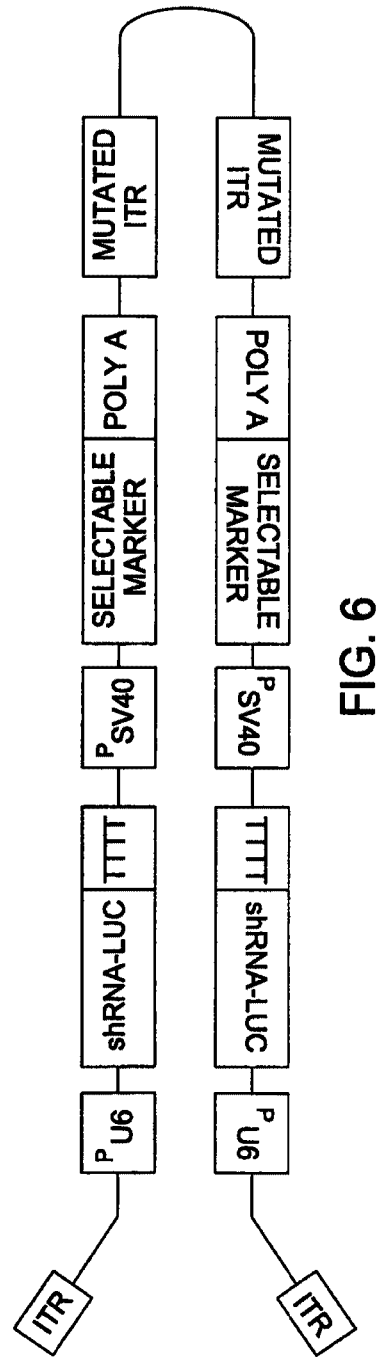
FIG. 5
FIG. 6

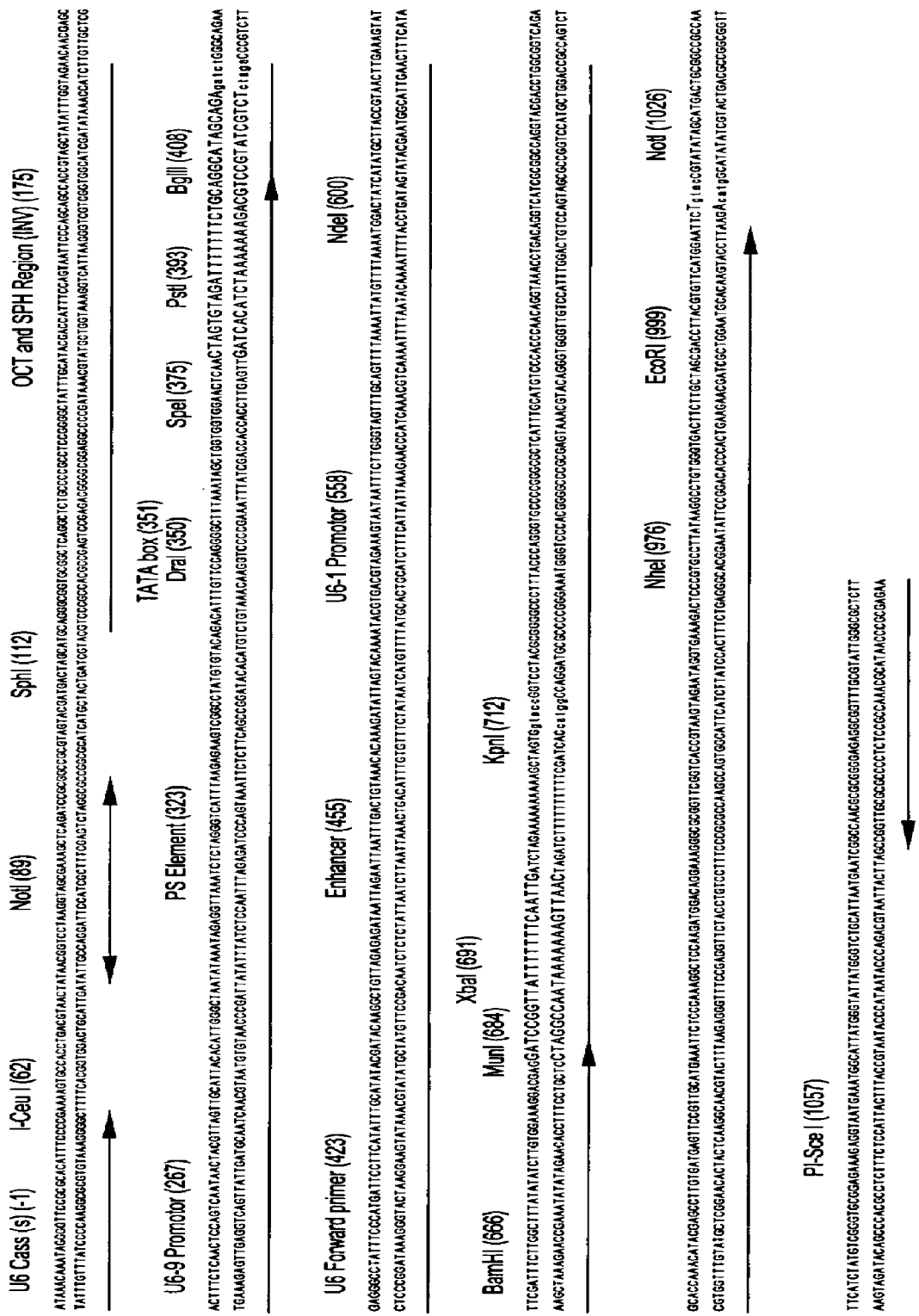

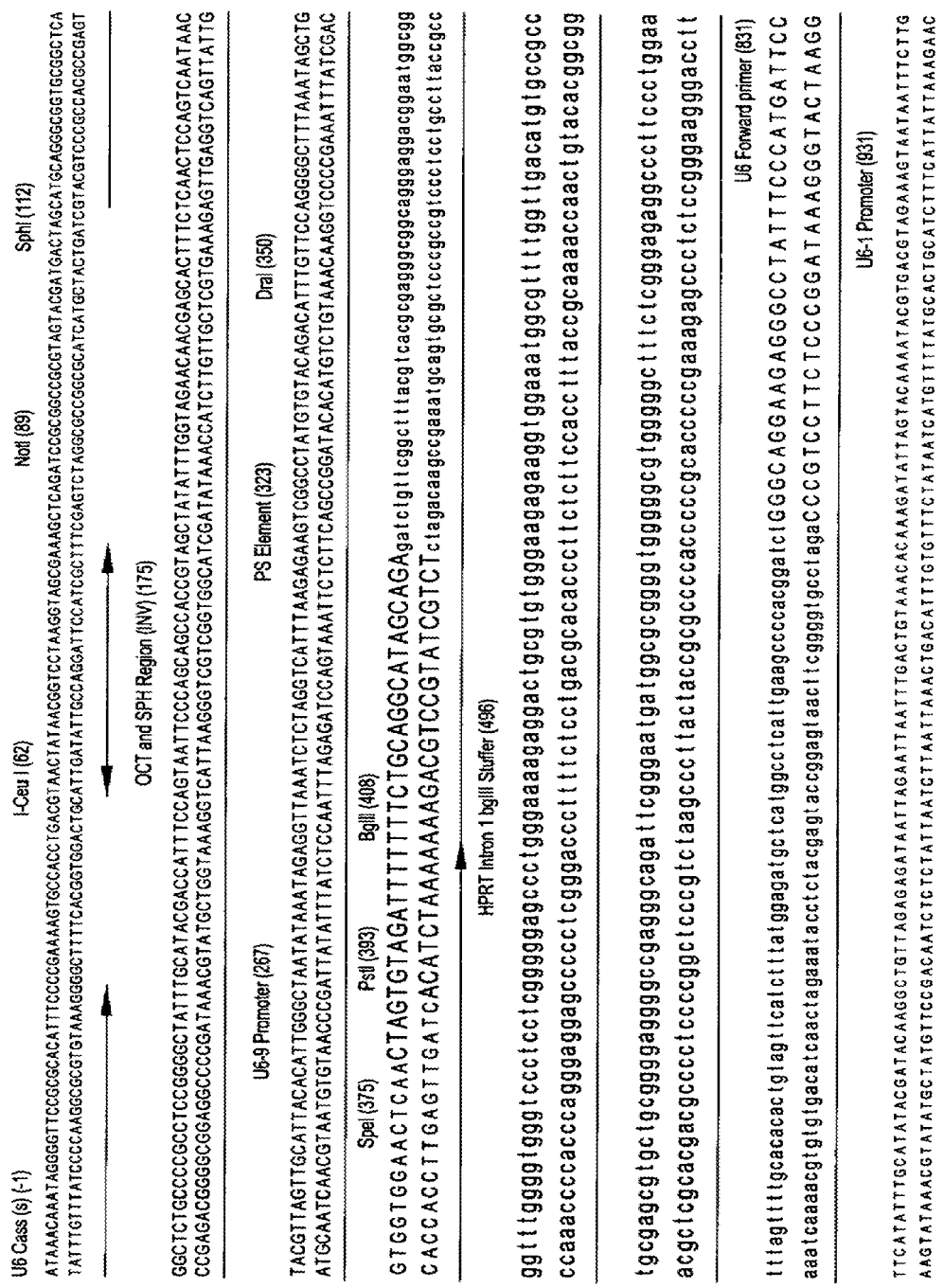

FIG. 11C

```
                                                                                              BamHI
         NdeI (1008)
GGTAGTTTGCAGTTTTAAAATTATGTTTAAAATTGGACTATCATATGCTTACCGTAACTTGAAAGTATTTCGATTTCTTGGCTTTATATATCTGTGGAAAGGACGAGGATCC
CCATCAAACGTCAAATTTTAATACAAATTTTAACCTGATAGTATACGAATGGCATTGAACTTTCATAAAGCTAAAGAACGAAATATATAGAACACCTTTCCTGCTCCTAGG

MunI (1092)
GGTTATTTTTTCaattgtacagctctggtagcggtaaccatgcgtatttgacacacgaaggaactagggaaaaggcattaggtcattcaagccga
CCAATAAAAAAAGttaacatgtcgagaccatcgccattggtacgcataaactgtgtgcttcctgatccctttccgtaatccagtaaagttcggct
                    HPRT Intron 1 MunI Stuffer (1233)
aattcacatgtgctagaatccagatccatgctgaccgatgcccaggatatagaaatgagaatctggtccttaccttcaagaacattcttaaccg
ttaagtgtacacgatcttaggtctaaggtacgactggctacggggtcctatatctttactcttagaccaggaatggaagttcttgtaacaattggc taatcagcctctggtatcttagctccaccctcactggttttcttgttgttgaaccggccaagctgctggcctccctcctcaaccgttctgatca
attagtcggagaccatagaatcgaggtgggagtgaccaaaaagaacaaacaacttggccggttcgacgaccggaggagttggcaagactagt tgcttgctaaatagtcaaaacccggccagttaaatgcttagcctgctcttattatgattattttttgttttggcaatgacctggctacctg
acgaacgattttatcagttttggggccggtcaattttatacgaaatcggacgaaataatactaataaaaacaacaaaaccgttactggaccgatggac
       XbaI (1508)                                                                  KpnI (1529)
ttgttttctcccactaaaactttttaagggcagggAATTGATCTAGAAAAAAAAAAAGCTAGTGtaccGGTCCTACGCGGGGCCCTTTACCCAGGGTCGCCCCGGCGC
aacaagaggggtgatttgaaaaattcccgtcccTTAACTAGATCTTTTTTTTCGATCACatgCCAGGATGCGCCCCGGGGAAATGGGTCCCACGGGGCCGGGG TCATTTGCATGTCCCACCCAACAGGTAAACCTGACAGGTCATCGCGGCAGTCTGACGCTGGCGTCAGAGCACCAAACATACGAGCCTTGTGATGAGTTCGTTGCATGAAAT
AGTAACGTACAGGGTGGGTTCGTCCATTGGACTGTCCAGTAGCGCCGGTCAGTCTCGTGGTTTGTATGCTCGGAACACTACTCAAGGGAACGTACTTTA
                                                                         NheI (1793)
     U6-8 promoter (1729)
TCTCCCAAAGGCTCCAAGATGGACAGGAAAGGCGCGGTTCGGTCACCGTAAGTAGAATAGGTGAAAGACTCCCGTGCCTTATAAGGCCTGTGGGTGACTTCTTGCTAGCGACC
AGAGGGTTTCCGAGGTTCTACCTGTCCTTCCCGCCCAAGCCAGTGGCCATTCATCTTATCCACTTTCTGAGGGCACGGAATATTCCGGACACCCACTGAAGAACGATCGGTGG EcoRI (1816)                           PI-SceI (1874)
TTACGTGTTCATGGAATTCTgtacCGTTATATAGCATGACTGGCCGTATAGCGATGCGGCCCAATTCATCTATGTGCGGGTGCGGAGAAAGAGGTAATGAAATGGCATTATGGGTCTGCATTAATGCGGCAAC
AATGCACAAGTACCTTAAGACatGGCATATATCGTACTGACTGCCGGCATATCGCTACGCCGGGTTAAGTAGATACAGCCCACGCCTCTTCCCATTACTTACGCGTAATACCAGAGACGTAATTACTTAGCCGGTTG

GCGCGGGGCGGTTTGCGTATTGGGCGCTCTT
CGCGCCCCGCCAAACGCATAACCCGCGAGAA
```

MULTIPLE PROMOTER EXPRESSION CASSETTES FOR SIMULTANEOUS DELIVERY OF RNAI AGENTS

CROSS-REFERENCE TO RELATED APPLICATIONS

This application claims benefit of U.S. application Ser. No. 11/072,592, filed Mar. 4, 2005, which in turn claims benefit of U.S. Provisional Patent Application Ser. No. 60/553,920, filed Mar. 17, 2004, and of U.S. Provisional Patent Application Ser. No. 60/550,504, filed Mar. 5, 2004, all of which are herein incorporated by reference.

BACKGROUND OF THE INVENTION

Utilization of double-stranded RNA to inhibit gene expression in a sequence-specific manner has revolutionized the drug discovery industry. In mammals, RNA interference, or RNAi, is mediated by 19- to 29-nucleotide long, double-stranded RNA molecules referred to as small interfering RNAs that are derived by enzymatic cleavage of long, double-stranded RNA within cells in vivo. RNAi agents can be synthesized chemically or enzymatically outside of cells and subsequently delivered to cells (see, e.g., Fire, et al., *Nature,* 391:806-11 (1998); Tuschl, et al., *Genes and Dev.,* 13:3191-97 (1999); and Elbashir, et al., *Nature,* 411:494-498 (2001)); or can be expressed in vivo by an appropriate vector in cells (see, e.g., McCaffrey, et al. *Nature Biotech.* 21(6): 639-644 (2003)).

However, in vivo delivery of unmodified RNAi as an effective therapeutic for use in humans faces a number of technical hurdles. First, due to cellular and serum nucleases, the half life of RNA injected in vivo is only about 70 seconds (see, e.g., Kurreck, *Eur. J. Bioch.* 270:1628-44 (2003)). Efforts have been made to increase stability of injected RNA by the use of chemical modifications; however, there are several occurrences in which chemical alterations led to increased cytotoxic effects. In one specific example, cells were intolerant to doses of an RNAi duplex in which every second phosphate was replaced by phosphorothioate (Harborth, et al., *Antisense Nucleic Acid Drug Rev.* 13(2): 83-105 (2003)). Other hurdles include providing tissue-specific delivery, as well as being able to deliver the RNAi agents in amounts sufficient to elicit a therapeutic response, but that are not toxic.

Several options are being explored for RNAi delivery, including the use of viral-based vector systems that can infect target cells, and deliver and express RNAi molecules in situ. Typically, small RNAs of approximately 70 nucleotides are transcribed as short hairpin precursors (shRNA) from a viral vector backbone. Once transcribed, the shRNA are processed by the enzyme Dicer into the appropriate active RNAi species. Viral-based delivery approaches attempt to exploit the targeting properties of viruses to generate tissue specificity and once appropriately targeted, rely upon the endogenous cellular machinery to generate sufficient levels of the RNAi species to achieve a therapeutically effective dose.

Currently, the most commonly used viruses for delivery of target sequences are those based upon systems evolved from retrovirus, herpes simplex virus (HSV) or adenovirus (Ad). All of these vectors can accommodate rather large inserts and can be produced in therapeutically relevant titers. However, in all systems, there are concerns relating to development of cancer (Cavazzana-Calvo, et al., *Science,* 288:669-72 (2000)), as well as undesirable host immune responses and resulting toxicity in patients. Another virus that is useful for delivering RNAi is adeno-associated virus (AAV).

One useful application of RNAi therapeutics is as an antiviral agent. In general, RNA viruses depend on RNA/DNA-dependent RNA polymerase for replication. Such RNA/DNA polymerases replicate the viral genome with comparatively low fidelity, the functional consequence of which produces genomes with an exceptionally high number of mutations. This results in the ability of rapidly evolving progeny virions to evade common immunological and chemical antiviral agents. Thus, similar to the effects observed with small molecule therapeutics, the relative potency and efficacy of the RNAi therapeutic may decrease as a result of viral evolution during long term treatment. In one study, HIV escape mutants that contained a single nucleotide change appeared 35 days after delivery of an expressed shRNA (Boden, et al., *J. Virol.* 77(21): 11531-11535 (2003)). In another study, poliovirus escape mutants could be detected in as little as 54 hours post-infection in cells that had been transfected with pre-synthesized RNAi. Yet, the simultaneous delivery of two RNAis against multiple target sequences within the virus significantly delayed the onset of escape variants (see Gitlin, et al., *Nature.* 418: 430-434 (2002)).

Thus, there is a need in the art to develop stable, effective RNAi therapeutics. The present invention satisfies this need in the art.

SUMMARY OF THE INVENTION

The present invention is directed to innovative compositions and methods for delivering RNAi species or agents to target cells. The RNAi species are part of a multiple promoter expression construct preferably delivered via a viral delivery system. Because three or more RNAi agents are used per construct, the present invention is particularly useful in addressing organisms with target genes that have sequence differences (SNPs) between variants, where each of the introduced RNAi agents can target one or more subset of variants. Similarly, the compositions and methods of the present invention are also useful in treating disease states caused by rapidly mutating pathogens, such as diseases caused by RNA-based viral agents; that is, it is less likely that viral escape mutants will be able to avoid the effect of three or more different RNAi sequences.

Thus, embodiments of the present invention provide a multiple promoter expression cassette comprising: at least three promoter/RNAi/terminator components, where each promoter/RNAi/terminator component comprises a promoter element, a terminator element, and an RNAi species operably linked to the promoter element and the terminator element, where the sequence of each of the RNAi species is different from one another. In various preferred aspects of this embodiment, the sequence of each of the promoter elements in the multiple-promoter expression cassette is different from one another. In other aspects of this embodiment, the sequence of each of the terminator elements in the multiple-promoter expression cassette is different from one another and/or each terminator element is taken from the same gene as the promoter element with which it is paired in nature. In addition, in one aspect of this embodiment, the present invention provides a multiple promoter expression construct that contains elements necessary for packaging of the therapeutic vector into infectious virus particles.

In another embodiment of the present invention, there is provided a method of treating one or more nucleic acid targets that are expressed in a cell comprising: incorporating a multiple promoter RNAi expression cassette that expresses three or more RNAi agents to inhibit one or more nucleic acid targets into a viral vector in order to produce a viral RNAi delivery construct; packaging the viral RNAi delivery construct into viral particles; delivering the viral particles to the cell; and expressing three or more RNAi agents from the multiple promoter expression cassette. In various aspects of this embodiment of the invention, the one or more nucleic acid targets that are expressed are genes necessary for the initiation or maintenance of a disease state, such as a cancerous state, in the cell. In other aspects of this embodiment of the invention, the one or more nucleic acid targets that are expressed are genes necessary for the infection or maintenance of infection of the cell by a pathogen. Alternatively, the multiple-promoter RNAi expression cassette may be provided in a non-viral vector and delivered to cells via non-viral methods known in the art.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

FIG. 5 is a schematic of one embodiment of a test recombinant AAV (rAAV) expression construct and a luciferase reporter construct.

FIG. 6 is a schematic of a self-complementary (scAAV) RNAi expression vector according to one embodiment of the present invention.

FIG. 11A is an example of a sequence (SEQ ID NO 31) of the triple promoter cassette type shown in FIG. 3B. FIGS. 11B/11C is an example of a sequence (SEQ ID NO 32) of the triple promoter cassette type shown in FIG. 3C.

DETAILED DESCRIPTION

Figure 1:
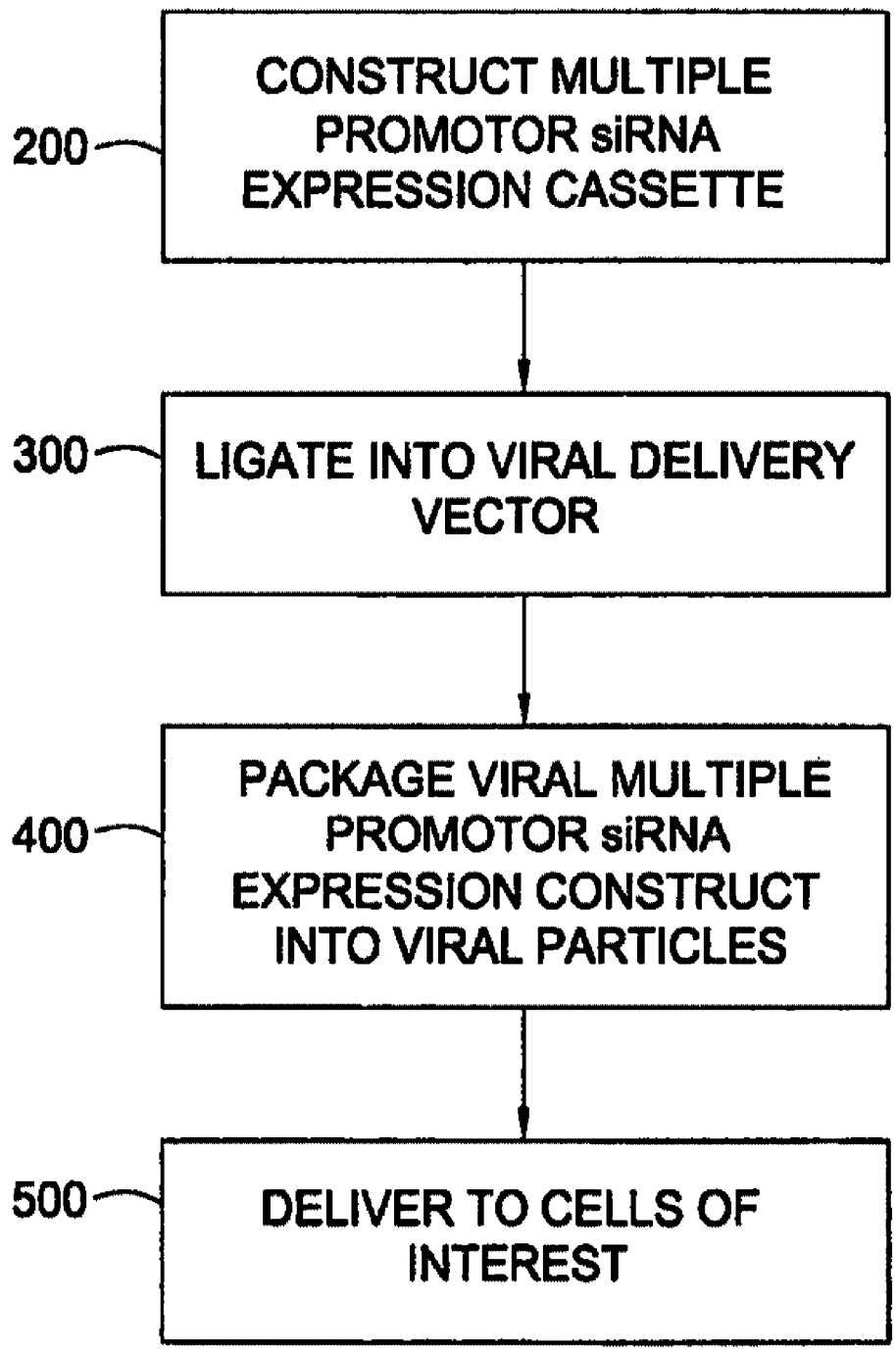
FIG. 1 is a simplified block diagram of one embodiment of a method for delivering RNAi species according to the present invention.

Before the present compositions and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

As used herein, the singular forms "a," "and," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference, without limitation, for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The present invention is directed to innovative, robust genetic compositions and methods to deliver at least three different RNAi agents simultaneously to a cell using a single expression construct. The compositions and methods provide stable, lasting inhibition of target nucleic acids.

Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, *Molecular Cloning: A Laboratory Manual* (1982); *DNA Cloning: A Practical Approach*, Volumes I and II (D. N. Glover, ed. 1985); *Oligonucleotide Synthesis* (M. J. Gait, ed. 1984); *Nucleic Acid Hybridization* (B. D. flames & S. J. Higgins, eds. (1984)); *Animal Cell Culture* (R. I. Freshney, ed. 1986); and *RNA Viruses: A practical Approach*, (Alan, J. Cann, Ed., Oxford University Press, 2000).

A "vector" is a replicon, such as plasmid, phage, viral construct or cosmid, to which another DNA segment may be attached. Vectors are used to transduce and express the DNA segment in cells.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III.

A cell has been "transformed", "transduced" or "transfected" by an exogenous or heterologous nucleic acid or vector when such nucleic acid has been introduced inside the cell, for example, as a complex with transfection reagents or packaged in viral particles. The transforming DNA may or may not be integrated (covalently linked) into the genome of the cell. With respect to eukaryotic cells, a stably transformed cell is one in which the transforming DNA has become integrated into a host cell chromosome or is maintained extrachromosomally so that the transforming DNA is inherited by daughter cells during cell replication or is a non-replicating, differentiated cell in which a persistent episome is present.

The term "RNA interference" or "RNAi" refers generally to a process in which a double-stranded RNA molecule or a short hairpin RNA changes the expression of a nucleic acid sequence with which they share substantial or total homology. The term "RNA species" or "RNAi agent" refers to a distinct RNA sequence that elicits RNAi; and the term "RNAi expression cassette" refers to a cassette according to embodiments of the present invention comprising three or more RNAi species.

FIG. 1 is a simplified flow chart showing the steps of one method 100 in which the multiple-promoter RNAi expression constructs according to the present invention may be used. First, in step 200, a multiple-promoter RNAi expression cassette targeting a particular disease target is constructed. Next, in step 300, the multiple-promoter RNAi expression cassette is ligated into an appropriate viral delivery construct. The viral RNAi expression delivery construct is then packaged into viral particles at step 400, and the viral particles are delivered to the target cells to be treated at step 500. Details for each of these steps and the components involved are presented infra.

The viral-based multiple-promoter RNAi expression constructs according to the present invention can be generated synthetically or enzymatically by a number of different protocols known to those of skill in the art and purified using standard recombinant DNA techniques as described in, for example, Sambrook et al., *Molecular Cloning: A Laboratory Manual,* 2nd Ed., Cold Spring Harbor Press, Cold Spring Harbor, N.Y. (1989), and under regulations described in, e.g., United States Dept. of HHS, National Institute of Health (NIH) Guidelines for Recombinant DNA Research. In a preferred embodiment, the multiple-promoter RNAi expression cassettes are synthesized using phosphoramidite, or analogous chemistry using protocols well known in the art.

Figure 2A:
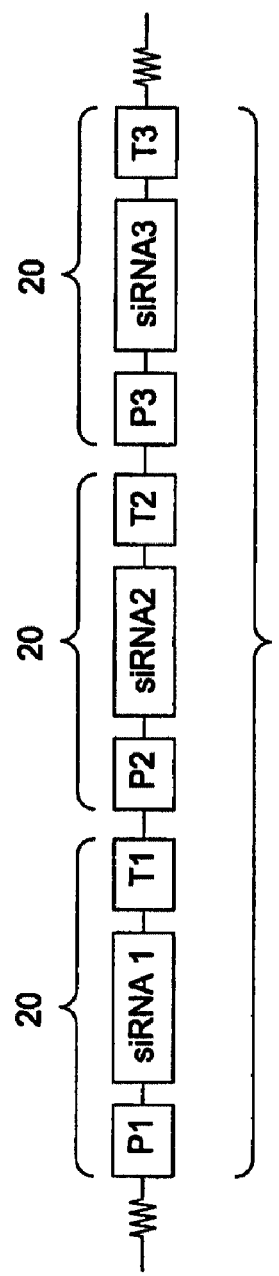
FIGS. 2A and 2B are simplified schematic representations of embodiments of the multiple-promoter RNAi expression cassette of the present invention.
Figure 2B:
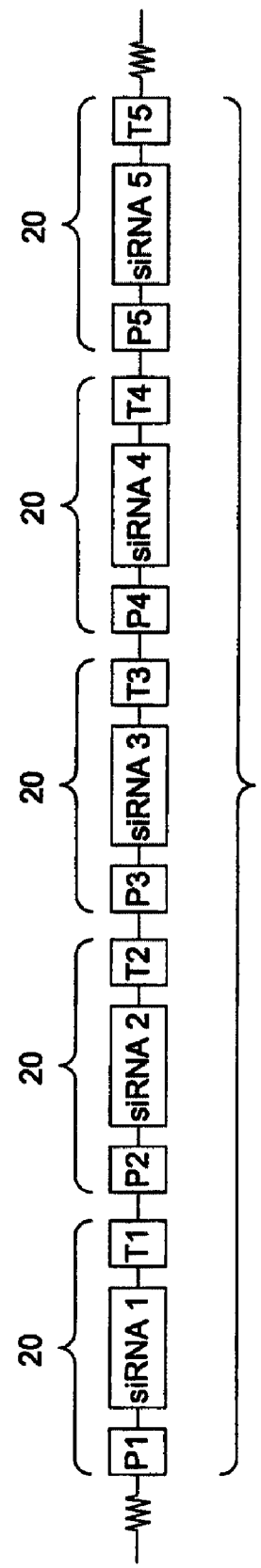

FIGS. 2A and 2B are simplified schematics of multiple-promoter RNAi expression cassettes according to embodiments of the present invention. FIG. 2A shows an embodiment of a multiple-promoter expression cassette (10) with three promoter/RNAi/terminator components (shown at 20), and FIG. 2B shows an embodiment of a multiple-promoter expression cassette (10) with five promoter/RNAi/terminator components (shown at 20). P1, P2, P3, P4 and P5 represent promoter elements. RNAi1, RNAi2, RNAi3, RNAi4 and RNAi5 represent sequences for five different RNAi species. T1, T2, T3, T4, and T5 represent termination elements. The multiple-promoter RNAi expression cassettes according to the present invention may contain three or more promoter/RNAi/terminator components where the number of promoter/RNAi/terminator components included in any multiple-promoter RNAi expression cassette is limited by, e.g., packaging size of the delivery system chosen (for example, some viruses, such as AAV, have relatively strict size limitations); cell toxicity, and maximum effectiveness (i.e. when, for example, expression of four RNAi sequences is as effective therapeutically as the expression of ten RNAi sequences).

The three or more RNAi species in the promoter/RNAi/terminator components comprising a cassette all have different sequences; that is RNAi1, RNAi2, RNAi3, RNAi4 and RNAi5 are all different from one another. However, the promoter elements in any cassette may be the same (that is, e.g., the sequence of two or more of P1, P2, P3, P4 and P5 may be the same); all the promoters within any cassette may be different from one another; or there may be a combination of promoter elements represented only once and promoter elements represented two times or more within any cassette.

Similarly, the termination elements in any cassette may be the same (that is, e.g., the sequence of two or more of T1, T2, T3, T4 and T5 may be the same, such as contiguous stretches of 4 or more T residues); all the termination elements within any cassette may be different from one another; or there may be a combination of termination elements represented only once and termination elements represented two times or more within any cassette. Preferably, the promoter elements and termination elements in each promoter/RNAi/terminator component comprising any cassette are all different to decrease the likelihood of DNA recombination events between components and/or cassettes. Further, in a preferred embodiment, the promoter element and termination element used in each promoter/RNAi/terminator component are matched to each other; that is, the promoter and terminator elements are taken from the same gene in which they occur naturally.

Figure 3A:
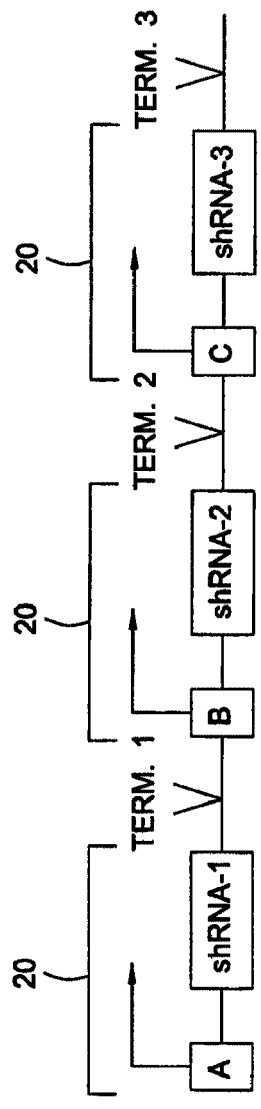
FIGS. 3A and 3B show two embodiments of multiple expression cassettes that deliver RNAi agents as shRNA precursors.
Figure 3B:
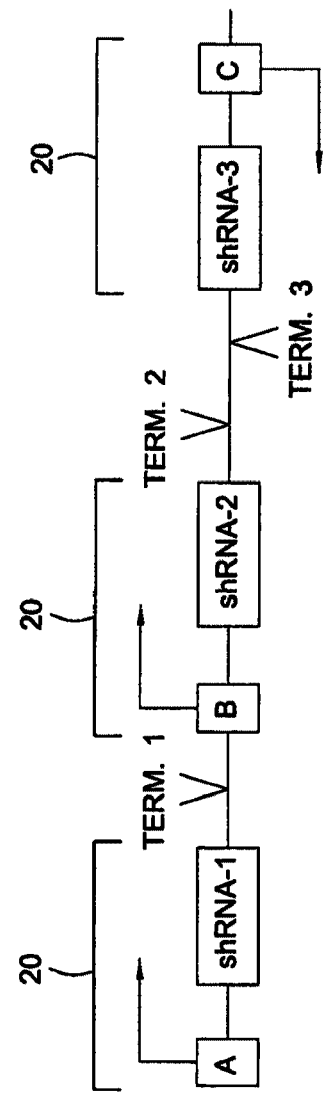
Figure 3C:
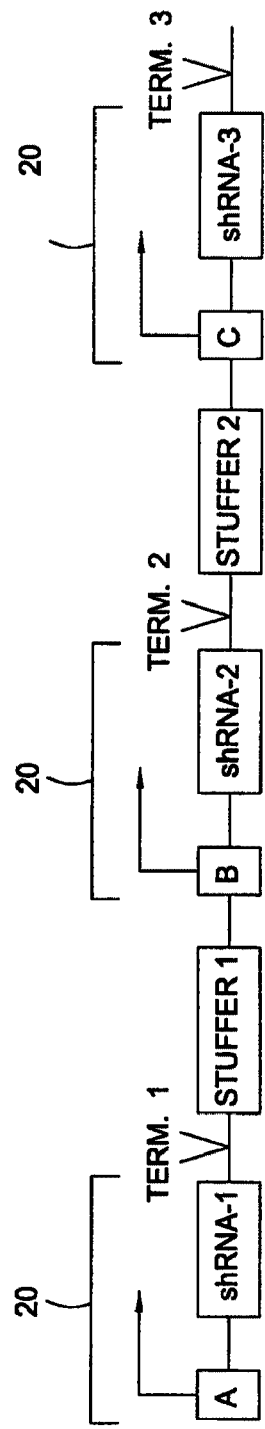
FIG. 3C shows an embodiment of a multiple expression cassettes comprising stuffer regions inserted between promoter/RNAi/terminator components.

FIGS. 3A, 3B and 3C show multiple-promoter RNAi expression constructs comprising alternative embodiments of multiple-promoter RNAi expression cassettes that express short shRNAs. shRNAs are short duplexes where the sense and antisense strands are linked by a hairpin loop. Once expressed, shRNAs are processed into RNAi species. Boxes A, B and C represent three different promoter elements, and the arrows indicate the direction of transcription. TERM 1, TERM 2, and TERM 3 represent three different termination sequences, and shRNA-1, shRNA-2 and shRNA-3 represent three different shRNA species. The multiple-promoter RNAi expression cassettes in the embodiments extend from the box marked A to the arrow marked Term3. FIG. 3A shows each of the three promoter/RNAi/terminator components (20) in the same orientation within the cassette, while FIG. 3B shows the promoter/RNAi/terminator components for shRNA-1 and shRNA-2 in one orientation, and the promoter/RNAi/terminator component for shRNA-3 in the opposite orientation (i.e., transcription takes place on both strands of the cassette).

FIG. 3C shows each of the cassettes separated by a region of DNA to increase the distance between promoter/RNAi/terminator components. The inserted DNA, known as "stuffer" DNA, can be any length between 5-5000 nucleotides. There can be one or more stuffer fragments between promoters. In the case of multiple stuffer fragments, they can be the same or different lengths. The stuffer DNA fragments are preferably different sequences. The stuffer DNA fragments may be used to increase the size of the multiple promoter cassette of the present invention in order to allow it to fit appropriately into a corresponding delivery vector. The length of the stuffer is dictated by the size requirements of the particular vector associated with the multiple promoter cassette. For example, in one embodiment the stuffer fragments total 4000 nucleotides (nt) in order to appropriately fulfill the size requirements of the AAV vector. In another embodiment, the stuffer fragments total 2000 nt in order to appropriately fulfill the size requirements of the self complementary AAV vector. Other variations may be used as well.

Figure 3D:
FIGS. 3D and 3E show embodiments of multiple-promoter RNAi expression cassettes that deliver RNAi without a shRNA precursor.
Figure 3E:
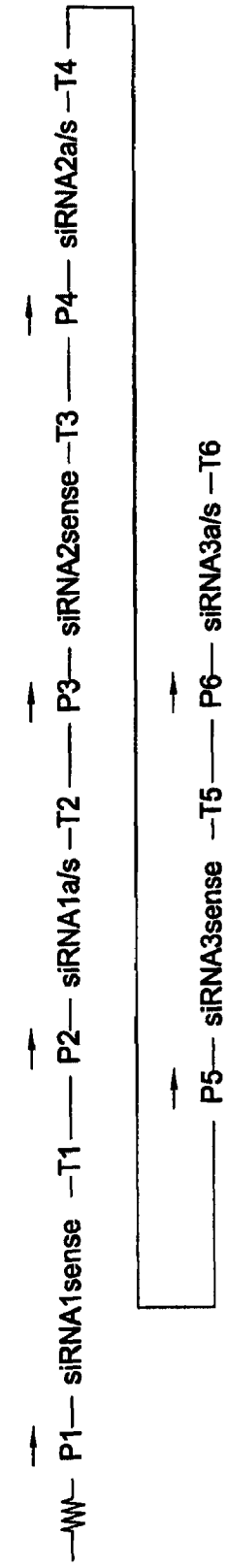

FIGS. 3D and 3E show multiple-promoter RNAi expression constructs comprising alternative embodiments of multiple-promoter RNAi expression cassettes that express RNAi species without a hairpin loop. In both figures, P1, P2, P3, P4, P5 and P6 represent promoter elements (with arrows indicating the direction of transcription); and T1, T2, T3, T4, T5, and T6 represent termination elements. Also in both Figures, RNAi1 sense and RNAi1 antisense (a/s) are complements, RNAi2 sense and RNAi2 a/s are complements, and RNAi3 sense and RNAi3 a/s are complements.

In the embodiment shown in FIG. 3D, all three RNAi sense sequences are transcribed from one strand (via P1, P2 and P3), while the three RNAi a/s sequences are transcribed from the complementary strand (via P4, P5, P6). In this particular embodiment, the termination element of RNAi1 a/s (T4) falls between promoter P1 and the RNAi1 sense sequence; while the termination element of RNAi1 sense (T1) falls between the RNAi1 a/s sequence and its promoter, P4. This motif is repeated such that if the top strand shown in FIG. 3D is designated the (+) strand and the bottom strand is designated the (−) strand, the elements encountered moving from left to right would be P1(+), T4(−), RNAi1 (sense and a/s), T1(+), P4(−), P2(+), T5(−), RNAi2 (sense and a/s), T2(+), P5(−), P3(+), T6(−), RNAi3 (sense and a/s), T3(+), and P6(−).

In an alternative embodiment shown in FIG. 3E, all RNAi sense and antisense sequences are transcribed from the same strand. One skilled in the art appreciates that any of the embodiments of the multiple-promoter RNAi expression cassettes shown in FIGS. 3A through 3E may be used for certain applications, as well as combinations or variations thereof.

In some embodiments, promoters of variable strength may be employed. For example, use of three or more strong promoters (such as a Pol III-type promoter) may tax the cell, by, e.g., depleting the pool of available nucleotides or other cellular components needed for transcription. In addition or alternatively, use of several strong promoters may cause a toxic level of expression of RNAi agents in the cell. Thus, in some embodiments one or more of the promoters in the multiple-promoter RNAi expression cassette may be weaker than other promoters in the cassette, or all promoters in the cassette may express RNAi agents at less than a maximum rate. Promoters also may or may not be modified using molecular techniques, or otherwise, e.g., through regulation elements, to attain weaker levels of transcription.

Promoters may be tissue-specific or cell-specific. The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., brain). Such tissue specific promoters include promoters such as Ick, myogenin, or thy1. The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue (see, e.g., Higashibata, et al., *J. Bone Miner. Res*. January 19(1):78-88 (2004); Hoggatt, et al., *Circ. Res*., December 91(12):1151-59 (2002); Sohal, et al., *Circ. Res. July* 89(1):20-25 (2001); and Zhang, et al., *Genome Res. January* 14(1):79-89 (2004)). The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a coding sequence in substantially any cell and any tissue. The promoters used to transcribe the RNAi species preferably are constitutive promoters, such as the promoters for ubiquitin, CMV, .beta.-actin, histone H4, EF-1 alfa or pgk genes controlled by RNA polymerase II, or promoter elements controlled by RNA polymerase I. In preferred embodiments, promoter elements controlled by RNA polymerase III are used, such as the U6 promoters (U6-1, U6-8, U6-9, e.g.), H1 promoter, 7SL promoter, the human Y promoters (hY1, hY3, hY4 (see Maraia, et al., *Nucleic Acids Res* 22(15):3045-52 (1994)) and hY5 (see Maraia, et al., *Nucleic Acids Res* 24(18):3552-59 (1994)), the human MRP-7-2 promoter, Adenovirus VA1 promoter, human tRNA promoters, the 5s ribosomal RNA promoters, as well as functional hybrids and combinations of any of these promoters.

Alternatively in some embodiments it may be optimal to select promoters that allow for inducible expression of the RNAi species. A number of systems for the inducible expression using such promoters are known in the art, including but not limited to the tetracycline responsive system and the lac operator-repressor system (see WO 03/022052 A1; and US 2002/0162126 A1), the ecdysone regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

One or more enhancers also may be present in the viral multiple-promoter RNAi expression construct to increase expression of the gene of interest. Enhancers appropriate for use in embodiments of the present invention include the Apo E HCR enhancer, the CMV enhancer that has been described recently (see, Xia et al, *Nucleic Acids Res* 31-17 (2003)), and other enhancers known to those skilled in the art.

In one embodiment this invention, ApoE enhancer elements may be added to the multiple promoter cassette of the present invention. The ApoE enhancer is an enhancer element of approximately 155 base pairs (bp) derived from apolipoprotein E or ApoE. One or more copies of the ApoE enhancer may be added upstream or downstream of the first, second and/or third promoters (or upstream or downstream of more than three promoters, if present) in the multiple promoter cassette of this invention. ApoE is an apolipoprotein that mediates binding, internalization and catabolism of lipoprotein particles and is a ligand for the low-density lipoprotein (ApoB/E) receptor and for the ApoE receptor of hepatic tissues. The genetic enhancer associated with the ApoE gene is a eukaryotic control element that can increase transcription of a nucleic acid specifically in the liver. The ApoE enhancer may be located up to 2000 nucleotides upstream or downstream of a liver-specific promoter, and may be present in one or more copies.

The RNAi sequences encoded by the multiple-promoter RNAi expression cassettes of the present invention result in the expression of small interfering RNAs that are short, double-stranded RNAs that are not toxic in mammalian cells. There is no particular limitation in the length of the RNAi species of the present invention as long as they do not show cellular toxicity. RNAis can be, for example, 15 to 49 bp in length, preferably 15 to 35 bp in length, and are more preferably 19 to 29 bp in length. The double-stranded RNA portions of RNAis may be completely homologous, or may contain non-paired portions due to sequence mismatch (the corresponding nucleotides on each strand are not complementary), bulge (lack of a corresponding complementary nucleotide on one strand), and the like. Such non-paired portions can be tolerated to the extent that they do not significantly interfere with RNAi duplex formation or efficacy.

The termini of an RNAi species according to the present invention may be blunt or cohesive (overhanging) as long as the RNAi effectively silences the target gene. The cohesive (overhanging) end structure is not limited only to a 3' overhang, but a 5' overhanging structure may be included as long as the resulting RNAi is capable of inducing the RNAi effect. In addition, the number of overhanging nucleotides may be any number as long as the resulting RNAi is capable of inducing the RNAi effect. For example, if present, the overhang may consist of 1 to 8 nucleotides; preferably it consists of 2 to 4 nucleotides.

The RNAi species utilized in the present invention may have a stem-loop structured precursor (shRNA) in which the ends of the double-stranded RNA are connected by a single-stranded, linker RNA. The length of the single-stranded loop portion of the shRNA may be 5 to 20 bp in length, and is preferably 5 to 9 bp in length.

Any transcribed nucleic acid sequence may be a target for the multiple-promoter RNAi expression cassettes of the present invention. Likely targets for the RNAi are genes such as but not limited to developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1, BCL1, BCL2, BCL6, CBFA2, CBL, CSF1R, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, and YES); tumor suppressor genes (e.g., APC, BRCA1, BRCA2, MADH4, MCC, NF1, NF2, RB1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); viral structural genes such as capsid and envelope proteins; bacterial genes such as those involved in replication or structural features, or genes from other pathogens that are involved in replication or structural features. In addition, the multiple-promoter RNAi expression cassettes of the present invention may be used to target specific sequences that are unique to alleles responsible for pathology in autosomal dominant diseases such as SCA, the allele responsible for Huntington's Disease, or the collagen gene alleles responsible for osteogenesis imperfecta. An important aspect of the invention is that viral infections cleared by siRNA can result in no harm to the infected cells (Gitlin, et. al. *Nature* 418: 430-434 (2002)). This feature of the present invention distinguishes it from prior art methods, where clearance of virus from the mammalian host causes destruction of infected cells, either by the action of the immune system or by apoptosis induced by the virus (Guidotti et. al. *Annu. Rev. Immunol.* 19: 65-91 (2001)). Thus, this aspect of the present invention provides an effective RNAi agent of noncytopathic viral clearance.

The sequences for the RNAi species are selected based upon the genetic sequence of the target nucleic acid sequence; and preferably are based on regions of target nucleic acid sequences that are conserved. For example, in the case of selecting RNAi sequences for treating a viral infection or for constructing an RNAi vaccine, the sequences chosen preferably are those that are conserved between species or even subspecies of the virus. As viruses are known to mutate rapidly, selection of conserved sequences is likely to preserve the efficacy of the RNAi over time. In the case of selection of RNAi sequences to treat cancer or other diseases, the sequences preferably are those that are conserved between variants of genes or oncogenes.

Methods of alignment of sequences for comparison and RNAi sequence selection are well known in the art. The determination of percent identity between two or more sequences can be accomplished using a mathematical algorithm. Preferred, non-limiting examples of such mathematical algorithms are the algorithm of Myers and Miller (1988); the search-for-similarity-method of Pearson and Lipman (1988); and that of Karlin and Altschul (1993). Preferably, computer implementations of these mathematical algorithms are utilized. Such implementations include, but are not limited to: CLUSTAL in the PC/Gene program (available from Intelligenetics, Mountain View, Calif.); the ALIGN program (Version 2.0), GAP, BESTFIT, BLAST, FASTA, Megalign (using Jotun Hein, Martinez, Needleman-Wunsch algorithms), DNAStar Lasergene (see www.dnastar.com) and TFASTA in the Wisconsin Genetics Software Package, Version 8 (available from Genetics Computer Group (GCG), 575 Science Drive, Madison, Wis., USA). Alignments using these programs can be performed using the default parameters or parameters selected by the operator. The CLUSTAL program is well described by Higgins. The ALIGN program is based on the algorithm of Myers and Miller; and the BLAST programs are based on the algorithm of Karlin and Altschul. Software for performing BLAST analyses is publicly available through the National Center for Biotechnology Information (http://www.ncbi.nlm.nih.gov/).

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Typically, inhibition of target sequences by RNAi requires a high degree of sequence homology between the target sequence and the sense strand of the RNAi molecules. In some embodiments, such homology is higher than about 70%, and may be higher than about 75%. Preferably, homology is higher than about 80%, and is higher than 85% or even 90%. More preferably, sequence homology between the target sequence and the sense strand of the RNAi is higher than about 90%, 91%, 92%, 93%, 94%, 95%, 96%, 97%, 98% or 99%. In embodiments where the multiple-promoter RNAi expression construct is used to target viral infections, it may be that sequence homology between the genomes of the various subspecies of the virus, even in conserved regions, does not reach the level of over 90% or even 80% over 15 to 30 consecutive nucleotides. In such a case, sequence homology between the target sequence for some subspecies and the sense strand of the RNAi may be 80% or less.

On the other hand, the multiple-promoter RNAi expression construct of the present invention is particularly useful when targeting genes of organisms that do not display high sequence homology across species, subspecies or variants, as each RNAi species in the multiple promoter RNAi expression cassette can be used to address different portions of the target gene(s) or subsets of variants or subspecies.

In addition to selecting the RNAi sequences based on conserved regions of a target sequence, selection of the RNAi sequences may be based on other factors. Despite a number of attempts to devise selection criteria for identifying sequences that will be effective in RNAi based on features of the desired target sequence (e.g., percent GC content, position from the translation start codon, or sequence similarities based on an in silico sequence database search for homologs of the proposed RNAi, thermodynamic pairing criteria), it is presently not possible to predict with much degree of confidence which of the myriad possible candidate RNAi sequences correspond to a desired target will, in fact, elicit an RNA silencing response. Instead, individual specific candidate RNAi polynucleotide sequences typically are generated and tested to determine whether interference with expression of a desired target can be elicited.

A major problem of current anti-viral therapies is the emergence of resistant variants, known generally as escape mutants (Gitlin et. al. *J. of Virol.* 79; 1027-1035, (2005)). One aspect of the present invention neutralizes emergent escape mutants. In some embodiments of this invention the selection of multiple RNAi sequences to treat viral infections is based on the emergence of escape mutants from treatment of infected cells with single sequence of RNAi. Emergent escape mutants are determined by treatment with an expression construct containing a single sequence of RNAi after the cells have been infected with virus. Cells containing resistant viruses that emerge are harvested and the viral genomes sequenced. Sequencing reveals predominant mutations that arise to resist viral inhibition. A multiple-promoter RNAi expression construct of the present invention is generated that contains RNAi sequences based upon the genetic sequence of the target gene and additionally sequences of the point mutations that arise to resist RNAi treatment.

As stated, the RNAi coding regions of the multiple-promoter RNAi expression cassette are operatively linked to terminator elements. In one embodiment, the terminators comprise stretches of four or more thymidine residues. In another preferred embodiment, the terminator elements used are all different and are matched to the promoter elements from the gene from which the terminator is derived. Such terminators include the SV40 poly A, the AdVA1 gene, the 5S ribosomal RNA gene, and the terminators for human t-RNAs. In addition, promoters and terminators may be mixed and matched, as is commonly done with RNA pol II promoters and terminators.

In addition, the multiple-promoter RNAi expression cassettes may be conFigured where multiple cloning sites and/or unique restriction sites are located strategically, such that promoter, RNAi and terminator elements are easily removed or replaced. Moreover, the multiple-promoter RNAi expression cassettes may be assembled from smaller oligonucleotide components using strategically located restriction sites and/or complementary sticky ends. The base vector for one approach according to embodiments of the present invention consists of plasmid with a multilinker in which all sites are unique (though this is not an absolute requirement). Sequentially, each promoter is inserted between its designated unique sites resulting in a base cassette with three promoters, or more, all of which can have variable orientation. Sequentially, again, annealed primer pairs are inserted into the unique sites downstream of each of the individual promoters, resulting in a triple expression cassette construct. The insert can be moved into, e.g. an AAV backbone using two unique enzyme sites (the same or different ones) that flank the triple expression cassette insert.

In step 300 of FIG. 1, the multiple-promoter RNAi expression cassettes are ligated into a delivery vector. The constructs into which the multiple-promoter RNAi expression cassette is inserted and used for high efficiency transduction and expression of the RNAi agents in various cell types preferably are derived from viruses and are compatible with viral delivery. Generation of the construct can be accomplished using any suitable genetic engineering techniques well known in the art, including without limitation, the standard techniques of PCR, oligonucleotide synthesis, restriction endonuclease digestion, ligation, transformation, plasmid purification, and DNA sequencing. The construct preferably comprises, for example, sequences necessary to package the multiple-promoter RNAi expression construct into viral particles and/or sequences that allow integration of the multiple promoter RNAi expression construct into the target cell genome. The viral construct also may contain genes that allow for replication and propagation of virus, though in preferred embodiments such genes will be supplied in trans. Additionally, the viral construct may contain genes or genetic sequences from the genome of any known organism incorporated in native form or modified. For example, the preferred viral construct comprises sequences useful for replication of the construct in bacteria.

The construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, or those coding for proteins that provide a biosynthetic capability missing from an auxotroph. If a reporter gene is included along with the multiple-promoter RNAi expression cassette, an internal ribosomal entry site (IRES) sequence can be included. Preferably, the additional genetic elements are operably linked with and controlled by an independent promoter/enhancer.

A viral delivery system based on any appropriate virus may be used to deliver the multiple-promoter RNAi expression constructs of the present invention. In addition, hybrid viral systems may be of use. The choice of viral delivery system will depend on various parameters, such as the tissue targeted for delivery, transduction efficiency of the system, pathogenicity, immunological and toxicity concerns, and the like. Given the diversity of disease targets that are amenable to interference by the multiple-promoter RNAi expression constructs of the present invention, it is clear that there is no single viral system that is suitable for all applications. When selecting a viral delivery system to use in the present invention, it is important to choose a system where multiple-promoter RNAi expression construct-containing viral particles are preferably: 1) reproducibly and stably propagated; 2) able to be purified to high titers; and 3) able to mediate targeted delivery (delivery of the multiple-promoter RNAi expression construct to the tissue or organ of interest without widespread dissemination); 4) able to be expressed in a constitutive or regulatable manner.

In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). This distinction is an important determinant of the suitability of each vector for particular applications; non-integrating vectors can, under certain circumstances, mediate persistent gene expression in non-proliferating cells, but integrating vectors are the tools of choice if stable genetic alteration needs to be maintained in dividing cells.

For example, in one embodiment of the present invention, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transducer a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai, et al., *J. Virol.* 76:11343-349 (2002). Expression of the transgene can be exceptionally stable and in one study with AAV delivery of Factor IX, a dog model continues to express therapeutic levels of the protein over 5.0 years after a single direct infusion with the virus. Because progeny virus is not produced from AAV infection in the absence of helper virus, the extent of transduction is restricted only to the initial cells that are infected with the virus. It is this feature which makes AAV a preferred gene therapy vector for the present invention. Furthermore, unlike retrovirus, adenovirus, and herpes simplex virus, AAV appears to lack human pathogenicity and toxicity (Kay, et al., *Nature.* 424: 251 (2003) and Thomas, et al., *Nature Reviews*, Genetics 4:346-58 (2003)).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order produce the proteins needed to replicate and package the AAV-based heterologous construct into nascent virion, the rep and cap proteins must be provided in trans. The helper functions normally provided by co-infection with the helper virus, such as adenovirus or herpesvirus mentioned above also can be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as RNAi.

The utility of AAV for RNAi applications was demonstrated in experiments where AAV was used to deliver shRNA in vitro to inhibit p53 and Caspase 8 expression (Tomar et al., *Oncogene.* 22: 5712-15 (2003)). Following cloning of the appropriate sequences into a gutted AAV-2 vector, infectious AAV virions were generated in HEK293 cells and used to infect HeLa S3 cells. A dose-dependent decrease of endogenous Caspase 8 and p53 levels was demonstrated. Boden et al. also used AAV to deliver shRNA in vitro to inhibit HIV replication in tissue culture systems (Boden, et al., *J. Virol.* 77(21): 115231-35 (2003)) as assessed by p24 production in the spent media.

However, technical hurdles must be addressed when using AAV as a vehicle for multiple-promoter RNAi expression constructs. For example, various percentages of the human population may possess neutralizing antibodies against certain AAV serotypes. However, since there are several AAV serotypes, some of which the percentage of individuals harboring neutralizing antibodies is vastly reduced, other serotypes can be used or pseudo-typing may be employed. There are at least eight different serotypes that have been characterized, with dozens of others which have been isolated but have been less well described. Another limitation is that as a result of a possible immune response to AAV, AAV-based therapy may only be administered once; however, use of alternate, non-human derived serotypes may allow for repeat administrations. Administration route, serotype, and composition of the delivered genome all influence tissue specificity.

Another limitation in using unmodified AAV systems with the multiple-promoter RNAi expression constructs is that transduction can be inefficient. Stable transduction in vivo may be limited to 5-10% of cells. However, different methods are known in the art to boost stable transduction levels. One approach is utilizing pseudotyping, where AAV-2 genomes are packaged using cap proteins derived from other serotypes. For example, by substituting the AAV-5 cap gene for its AAV-2 counterpart, Mingozzi et al. increased stable transduction to approximately 15% of hepatocytes (Mingozzi, et al., *J. Virol.* 76(20): 10497-502 (2002)). Thomas et al., transduced over 30% of mouse hepatocytes in vivo using the AAV8 capsid gene (Thomas, et al., *J. Virol.* in press). Grimm et al. (*Blood.* 2003-02-0495) exhaustively pseudotyped AAV-2 with AAV-1, AAV-3B, AAV-4, AAV-5, and AAV-6 for tissue culture studies. The highest levels of transgene expression were induced by virion which had been pseudotyped with AAV-6; producing nearly 2000% higher transgene expression than AAV-2. Thus, the present invention contemplates use of a pseudotyped AAV virus to achieve high transduction levels, with a corresponding increase in the expression of the RNAi multiple-promoter expression constructs.

Another viral delivery system useful with the multiple-promoter RNAi expression constructs of the present invention is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some embodiments, lentiviruses are the preferred members of the retrovirus family for use in the present invention. Lentivirus vectors are often pseudotyped with vesicular steatites virus glycoprotein (VSV-G), and have been derived from the human immunodeficiency virus (HIV), the etiologic agent of the human acquired immunodeficiency syndrome (AIDS); visan-maedi, which causes encephalitis (visna) or pneumonia in sheep; equine infectious anemia virus (EIAV), which causes autoimmune hemolytic anemia and encephalopathy in horses; feline immunodeficiency virus (Hy), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization.

Reverse transcription of the retroviral RNA genome occurs in the cytoplasm. Unlike C-type retroviruses, the lentiviral cDNA in complexes with other viral factors—known as the pre-initiation complex—is able to translocate across the nuclear membrane and transduce non-dividing cells. A structural feature of the viral cDNA—a DNA flap—seems to contribute to efficient nuclear import. This flap is dependent on the integrity of a central polypurine tract (cPPT) that is located in the viral polymerase gene, so most lentiviral-derived vectors retain this sequence. Lentiviruses have broad tropism, low inflammatory potential, and result in an integrated vector. The main limitations are that integration might induce oncogenesis in some applications. The main advantage to the use of lentiviral vectors is that gene transfer is persistent in most tissues or cell types.

A lentiviral-based construct used to express the RNAi agents preferably comprises sequences from the 5' and 3' long terminal repeats (LTRs) of a lentivirus. More preferably the viral construct comprises an inactivated or self-inactivating 3' LTR from a lentivirus. The 3' LTR may be made self-inactivating by any method known in the art. In a preferred embodiment, the U3 element of the 3' LTR contains a deletion of its enhancer sequence, preferably the TATA box, Sp1 and NF-kappa B sites. As a result of the self-inactivating 3' LTR, the provirus that is integrated into the host genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the multiple-promoter RNAi expression cassettes of the present invention to cells of interest, including but not limited to gene-deleted adenovirus-transposon vectors that stably maintain virus-encoded transgenes in vivo through integration into host cells (see Yant, et al., *Nature Biotech.* 20:999-1004 (2002)); systems derived from Sindbis virus or Semliki forest virus (see Perri, et al, *J. Virol.* 74(20):9802-07 (2002)); systems derived from Newcastle disease virus or Sendai virus; or mini-circle DNA vectors devoid of bacterial DNA sequences (see Chen, et al., *Molecular Therapy.* 8(3):495-500 (2003)). Mini-circle DNA as described in U.S. Publ. No. 2004/0214329 discloses vectors that provide for persistently high levels of nucleic acid transcription. The circular vectors are characterized by being devoid of expression-silencing bacterial sequences, and may include a unidirectional site-specific recombination product sequence in addition to an expression cassette.

In addition, hybrid viral systems may be used to combine useful properties of two or more viral systems. For example, the site-specific integration machinery of wild-type AAV may be coupled with the efficient internalization and nuclear targeting properties of adenovirus. AAV in the presence of adenovirus or herpesvirus undergoes a productive replication cycle; however, the in the absence of helper functions, the AAV genome integrates into a specific site on chromosome 19. Integration of the AAV genome requires expression of the AAV rep protein. As conventional AAV vectors are deleted for all viral genes including rep, they are not able to specifically integrate into chromosome 19. However, this feature may be exploited in an appropriate hybrid system. In addition, non-viral genetic elements may be used to achieve desired properties in a viral delivery system, such as genetic elements that allow for site-specific recombination.

Figure 4A:
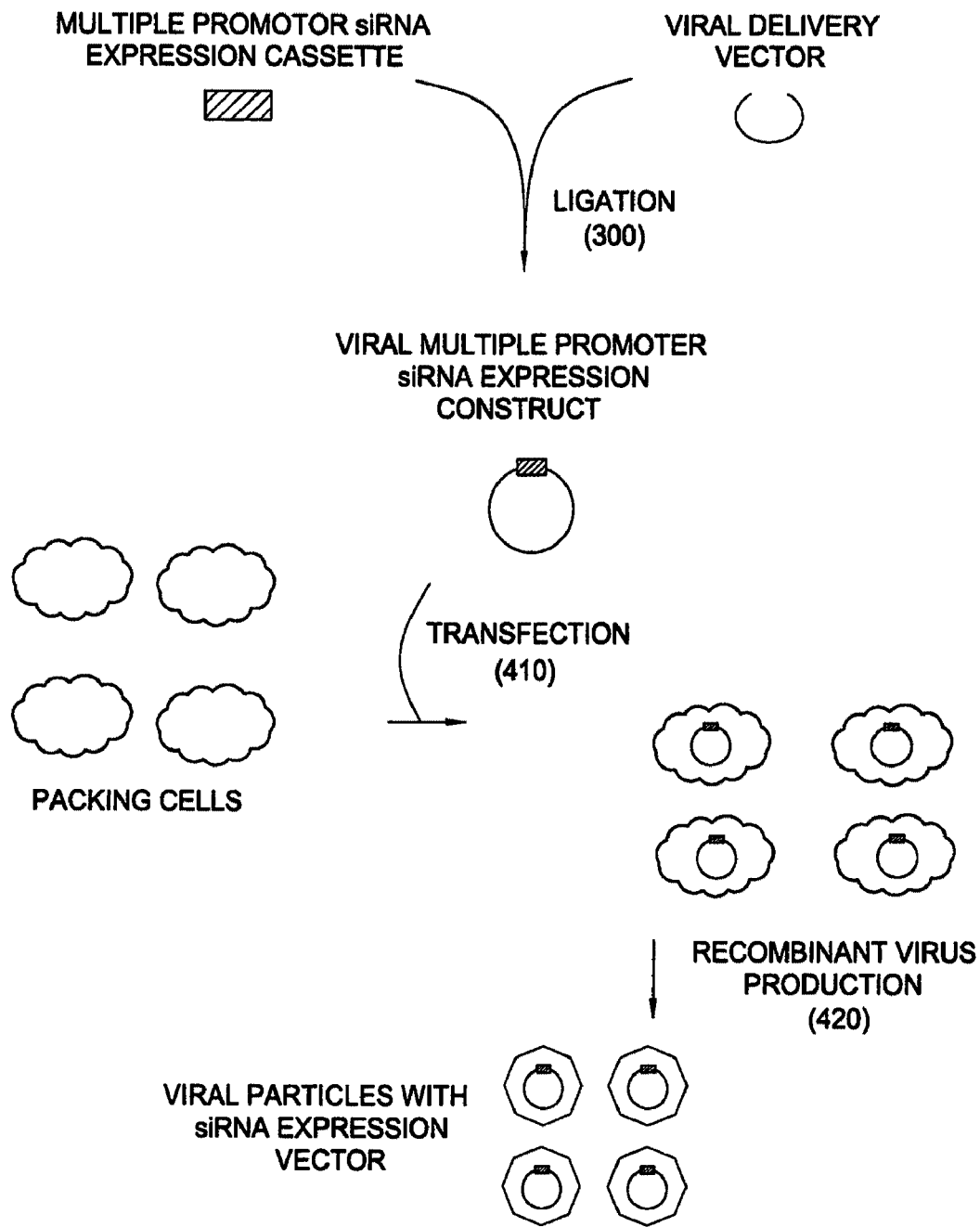
FIG. 4A is a simplified representation of one method of producing multiple-promoter RNAi expression vectors packaged in viral particles.
Figure 4B:
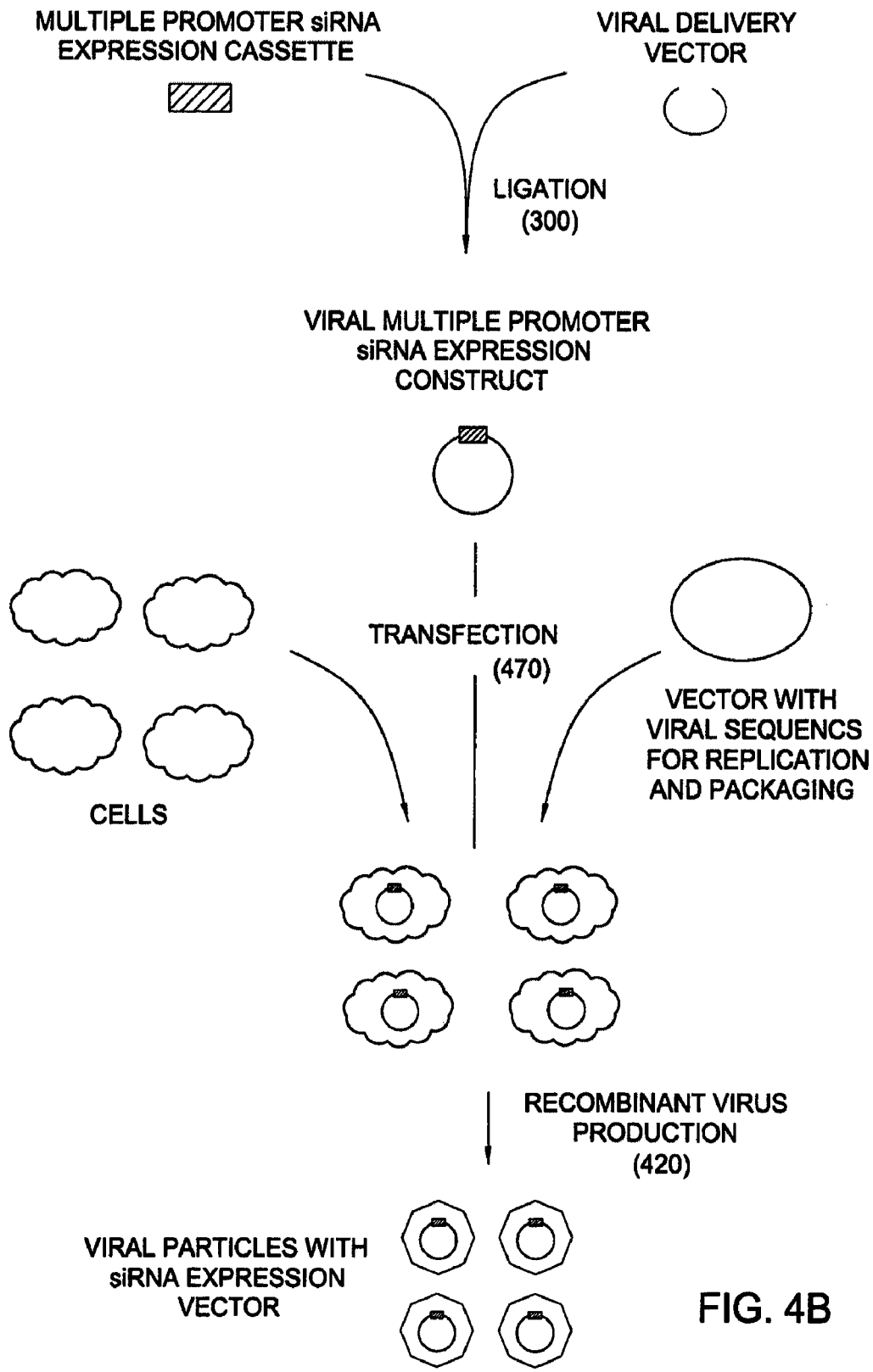
FIG. 4B is a simplified representation of another method of producing multiple-promoter RNAi expression vectors packaged in viral particles.

In step 400 of FIG. 1, the multi-promoter RNAi expression construct is packaged into viral particles. Any method known in the art may be used to produce infectious viral particles whose genome comprises a copy of the viral multiple-promoter RNAi expression construct. FIGS. 4A and 4B show alternative methods for packaging the multiple-promoter RNAi expression constructs of the present invention into viral particles for delivery. The method in FIG. 4A utilizes packaging cells that stably express in trans the viral proteins that are required for the incorporation of the viral multiple-promoter RNAi expression construct into viral particles, as well as other sequences necessary or preferred for a particular viral delivery system (for example, sequences needed for replication, structural proteins and viral assembly) and either viral-derived or artificial ligands for tissue entry. In FIG. 4A, a multiple-promoter RNAi expression cassette is ligated to a viral delivery vector (step 300), and the resulting viral multiple-promoter RNAi expression construct is used to transfect packaging cells (step 410). The packaging cells then replicate viral sequences, express viral proteins and package the viral multiple-promoter RNAi expression constructs into infectious viral particles (step 420). The packaging cell line may be any cell line that is capable of expressing viral proteins, including but not limited to 293, HeLa, A549, PerC6, D17, MDCK, BHK, bing cherry, *phoenix*, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with two or more constructs to achieve efficient production of functional particles. One of the constructs comprises the viral multiple-promoter RNAi expression construct, and the other plasmid(s) comprises nucleic acids encoding the proteins necessary to allow the cells to produce functional virus (replication and packaging construct) as well as other helper functions. The method shown in FIG. 4B utilizes cells for packaging that do not stably express viral replication and packaging genes. In this case, the promoter RNAi expression construct is ligated to the viral delivery vector (step 300) and then co-transfected with one or more vectors that express the viral sequences necessary for replication and production of infectious viral particles (step 430). The cells replicate viral sequences, express viral proteins and package the viral multiple-promoter RNAi expression constructs into infectious viral particles (step 420).

The packaging cell line or replication and packaging construct may not express envelope gene products. In these embodiments, the gene encoding the envelope gene can be provided on a separate construct that is co-transfected with the viral multiple-promoter RNAi expression construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells.) In addition, genetically-modified ligands can be used for cell-specific targeting, such as the asialoglycoprotein for hepatocytes, or transferrin for receptor-mediated binding.

After production in a packaging cell line, the viral particles containing the multiple-promoter RNAi expression cassettes are purified and quantified (titered). Purification strategies include density gradient centrifugation, or, preferably, column chromatographic methods.

The viral multiple-promoter RNAi expression cassettes of the present invention are particularly useful as therapeutics to treat disease or as vaccines to prevent disease. For example, the multiple-promoter RNAi expression constructs may be introduced into a cancerous cell or tumor to inhibit expression of a gene required for maintenance of the carcinogenic/tumorigenic phenotype. Similarly, the multiple-promoter RNAi expression constructs may be introduced into a cell infected with a pathogen such as a virus to inhibit gene expression of one or more genes required for maintenance of the pathogen. To prevent a disease or other pathology, a multiple-promoter RNAi expression construct may be used as a vaccine to target a gene required for initiation or maintenance of the disease or pathology.

The viral multiple-promoter RNAi expression constructs of the present invention may be used in the treatment of cancer, including solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), hystiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pheochromocytoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. In addition, the multiple-promoter RNAi expression constructs of the present invention could be used in combination with other treatment modalities, such as chemotherapy, surgical intervention, cryotherapy, hyperthermia, radiation therapy, and the like.

A gene involved in the replication of a pathogen, transmission of a pathogen, or maintenance of infection may be targeted by the viral multiple-promoter RNAi expression constructs. Such viral multiple-promoter RNAi expression constructs may be used to treat cells at risk for infection by a pathogen (i.e., vaccine) or cells that already have been infected. Pathogens that may be treated by the multiple-promoter RNAi expression constructs and methods of the present invention include viruses from the families Parvoviridae, Papovaviridae (including Papilloma virus, etc.), Adenoviridae, Herpesviridae (including herpesvirus types 1 through 7), Poxyiridae, Hepadnaviridae, Picornaviridae (coxsackie A and coxsackie B viruses and ECHOvirus), Caliciviridae, Reoviridae, Togaviridae (encephalitis viruses), Flaviviridae (encephalitis viruses), Arenaviridae, Retroviridae, Bunyaviridae, Coronaviridae, Orthomyzoviridae, Paramyxoviridae, Rhabdoviridae and Filoviridae, bacteria generally, mycobacteria, fungi, *Falciparum, Tryponosoma Schistosoma*, and the like.

In step 500 of FIG. 1, the multiple-promoter RNAi expression construct is delivered to the cells to be treated. The multiple-promoter RNAi expression construct of the present invention may be introduced into the cells in vitro or ex vivo and then subsequently placed into an animal to affect therapy, or administered directly to an organism, organ or cell by in vivo administration. Delivery by viral infection is a preferred method of delivery; however, any appropriate method of delivery of the multiple-promoter RNAi expression construct may be employed. The vectors comprising the multiple-promoter cassettes can be administered to a mammalian host using any convenient protocol, where a number of different such protocols are known in the art.

The nucleic acids may be introduced into tissues or host cells by any number of routes, including viral infection, microinjection, or fusion of vesicles. Injection may also be used for intra-muscular administration, as described by Furth et al., *Anal. Biochem.* 115(205):365-368 (1992). The nucleic acids may be coated onto gold microparticles, and delivered intradermally by a particle bombardment device, or "gene gun" as described in the literature (see, for example, Tang et al., *Nature.* 356:152-154 (1992)), where gold microprojectiles are coated with the DNA, then bombarded into skin cells.

Another delivery method useful for the method of the present invention comprises the use of Cyclosert™ technology as described in U.S. Pat. No. 6,509,323 to Davis et. al. Cyclosert™ technology platform is based upon cup-shaped cyclic repeating molecules of glucose known as cyclodextrins. The "cup" of the cyclodextrin molecule can form "inclusion complexes" with other molecules, making it possible to combine the Cyclosert™ polymers with other moieties to enhance stability or to add targeting ligands. In addition, cyclodextrins generally have been found to be safe in humans (individual cyclodextrins currently enhance solubility in FDA-approved oral and IV drugs) and can be purchased in pharmaceutical grade on a large scale at low cost. These polymers are extremely water soluble, non-toxic and non-immunogenic at therapeutic doses, even when administered repeatedly. The polymers can easily be adapted to carry a wide range of small-molecule therapeutics at drug loadings that can be significantly higher than liposomes.

The vectors comprising the multiple-promoter cassettes can be formulated into preparations for injection or administration by dissolving, suspending or emulsifying them in an aqueous or nonaqueous solvent, such as oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In addition, the vectors comprising the multiple-promoter cassettes can be formulated into pharmaceutical compositions by combination with appropriate, pharmaceutically acceptable carriers or diluents. In pharmaceutical dosage forms, the vectors comprising the multiple-promoter cassettes may be administered alone or in association or combination with other pharmaceutically active compounds. Those with skill in the art will appreciate readily that dose levels for vectors comprising the multiple-promoter cassettes will vary as a function of the nature of the delivery vehicle, the relative ease of transduction of the target cells, the expression level of the RNAi species in the target cells and the like.

EXAMPLES

One disease state that may be treated with the multiple-promoter RNAi expression constructs of the present invention is hepatitis C virus (HCV) infection. Based on statistics compiled from the Centers for Disease Control and Prevention, almost 2% of the American population—nearly 4 million people—is currently infected with HCV. Initially, the majority of the individuals infected with HCV exhibit no symptoms; however, greater than 80% will develop chronic and progressive liver disease eventually leading to cirrhosis or hepatocellular carcinomas. HCV is the leading indication for liver transplantation within the United States and results in the death of 8,000 to 10,000 Americans every year. On a global level, the World Heath Organization estimates that there are more than 170 million affected individuals, with infection rates as high as 10-30% of the general population in some countries.

HCV is a positive-sense single stranded enveloped RNA virus belonging to the Flaviviridae family. The infectious cycle of HCV typically begins with the entry of the viral particle into the cell by receptor-mediated binding and internalization. After uncoating in the cytoplasm, the positive strand of RNA that comprises the genome can interact directly with the host cell translational machinery. Lacking 5' cap methylation, the RNA forms an extensive secondary structure in the 5' Untranslated Region (UTR) that serves as an internal ribosomal entry site (IRES) and permits the direct binding of the 40S subunit as the initiating step of the translation process.

Figure 8A:
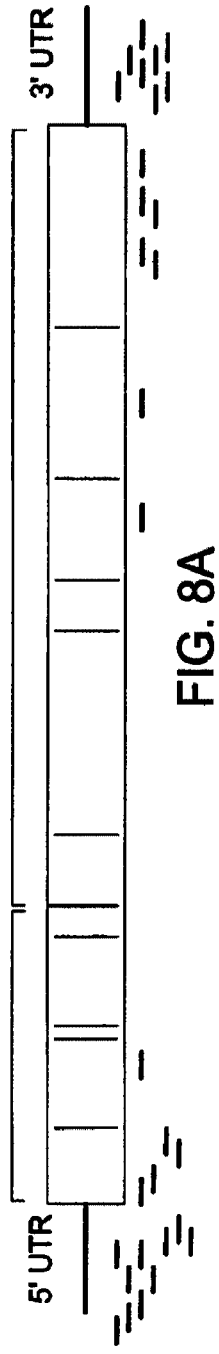
FIG. 8A is a schematic of the HCV genome showing the position of RNAi agents tested in experiments described herein. 8B is a schematic of a luciferase-HCV fusion replicon containing genetic elements for non-structural proteins. 8C is a schematic of a luciferase-HCV fusion replicon containing HCV genetic elements for structural and non-structural proteins.

The HCV genome, approximately 9600 nucleotides in length, encodes a single long open reading frame termed the polyprotein (shown in FIG. 8A). Viral proteins are produced as linked precursors from the polyprotein which is subsequently cleaved into mature products by a wide variety of viral and cellular enzymes. Encoded amongst the genes are the structural proteins, including the core and envelope glycoproteins, so named because they are integral structural components in progeny virions. Non-structural proteins, which provide indispensable functions such as the RNA-dependent RNA polymerase, are also produced. The viral replication machinery is established within the cytoplasm of infected cells that transcribe the positive-sense RNA into a negative strand intermediate. Thus, the HCV genomic RNA serves as both a template for its own replication and as a messenger RNA for translation of the virally encoded proteins. The negative strand is transcribed back into a positive strand of RNA, thereby amplifying the number of positive strand copies within the cell. At this stage, the positive strand can interact with the host cell translational machinery once again or, if there have been enough structural proteins accumulated, be packaged into virions. Following egress from the cell, the virus repeats its infectious cycle.

Example 1

Development of an AAV-2 Expression Vector for In Vivo Delivery of shRNA Sequences Before the delivery of shRNA by infectious particles is tested, the appropriate expression plasmid is constructed and validated. There are at least two characteristics that can be considered when designing the multiple-promoter RNAi expression construct: 1) the construct must be efficiently packaged into progeny virion; and 2) the plasmid must provide high levels of shRNA expression. In addition, in order to test the various multiple-promoter RNAi expression constructs, there must be a means of assessing transfection and transduction efficiency.

AAV-2 vectors which have been gutted of rep and cap sequence provide the backbone (hereinafter referred to as the rAAV vector) for the viral RNAi expression construct. This vector has been extensively employed in AAV studies and the requirements for efficient packaging are well understood. The U6 and H1 promoters are used for the expression of shRNA sequences, though there have been reports of vastly different levels of inhibition of an identical shRNA driven independently by each promoter. However, vector construction is such that promoters can be easily swapped if such variation is seen.

As with virtually any viral delivery system, the rAAV vector must meet certain size criteria in order to be packaged efficiently. In general, an rAAV vector must be 4300-4900 nucleotides in length (McCarty, et al. *Gene Ther.* 8: 1248-1254 (2001)). When the rAAV vector falls below the limit, a 'stuffer' fragment must be added (Muzyczka, et al. *Curr. Top. Microbiol. Immunol.* 158: 970129 (1992)). Alternatively, the rAAV multiple-promoter RNAi expression construct may be filled out with two or more multiple-promoter RNAi expression cassettes.

In the rAAV vector embodiment described here, each promoter/RNAi/terminator component is approximately 400 nucleotides in length, leaving ample room for the inclusion of many promoter/RNAi/terminator components per expression cassette. Alternatively, one or more selectable marker cassettes may be engineered into the rAAV multiple-promoter RNAi expression construct in order to assess the transfection efficiency of the rAAV expression construct as well as allow for quantification of transduction efficiency of target cells by the rAAV expression construct delivered via infectious particles.

The initial test expression construct drives expression of a shRNA species designed from sequences with demonstrated ability to inhibit luciferase activity from a reporter construct (See, Elbashir, et al. *Embo. J.* 20(23): 6877-6888 (2001)). The elements of the RNAi cassette, including the promoter, shRNA and the terminator sequence, are short and are assembled independently de novo utilizing long, complementary oligonucleotides that are then cloned into a viral vector using multiple cloning sites. A commercially available expression plasmid that encodes for the production of luciferase functions as the reporter in order to verify the ability of the shRNA to down regulate the target sequences (as shown in FIG. 5).

Although the shRNA against luciferase has been previously validated, the efficacy of rAAV-delivered shRNA is assessed in vitro prior to testing the construct in vivo. The test and reporter constructs are transfected into permissive cells utilizing standard techniques. An rAAV expression construct in which the luciferase-specific shRNA has been replaced by an unrelated shRNA sequence is utilized as a negative control in the experiments. The relative percentage of transfection efficiency is estimated directly by assessing the levels of the selective marker using fluorescence microscopy. For assessing inhibitory activity of the shRNA, luciferase activity is measured utilizing standard commercial kits. Alternatively, quantitative real time PCR analysis (Q-PCR) is run on RNA that is harvested and purified from parallel experimental plates. Activity decreases greater than 90% percent, relative to the activity recovered in lysates from cells treated with the unrelated shRNA species, are an indication that the shRNA is highly functional.

Subsequent experiments are performed in order to assess the effects of shRNA on a luciferase reporter system that is transfected into the livers of mice, similar to the work of McCaffrey et al. in *Nature.* 418: 38-39 (2002). Nucleic acids delivered to mice by hydrodynamic transfection methods (high pressure tail vein injection) primarily localized to the livers. Much like the principle which governs co-transfection in cell culture, simultaneous injection of multiple plasmids from a mixture often permits the penetration of all of the expression constructs into the same cell. Thus, even though the tail vein injection procedures are well documented to only transfect 5-40% of the hepatocytes within the liver (McCaffrey, et al. *Nature Biotech.* 21(6): 639-644 (2003)), co-injection permits delivery of the reporter system and the expression construct into the same cells.

The rAAV expression construct bearing the shRNA sequence targeted against luciferase is co-injected with the reporter construct that encodes for the luciferase gene. In animals receiving the negative control, an expression construct bearing an unrelated shRNA is co-injected with the reporter construct. After seven days, the mice are sacrificed and the livers harvested. Luciferase activity is measured on lysates generated from a portion of the liver. Remaining portions of the liver are utilized for Q-PCR measurements as well as histological analysis to determine marker protein expression for normalization of the data. Alternative methods to assess transfection efficiency may include ELISA measurements of serum from mice that have been co-injected with a third marker plasmid for a secreted protein such as human .alpha.1-antitrypsin (hAAT) (Yant, et al. *Nature Genetics.* 25: 35-41 (2000), see also McCaffrey, et al. *Nature Biotech.* 21(6): 639-644 (2003)).

Once it is established that the expression construct is functional in both in vitro cell culture systems as well as in vivo mouse models by utilizing co-transfection of the naked DNA plasmids, testing is initiated on the rAAV expression construct packaged into infectious particles. The infectious particles are produced from a commercially available AAV helper-free system that requires the co-transfection of three separate expression constructs containing 1) the rAAV construct expressing the shRNA against luciferase (flanked by the AAV ITRs); 2) the construct encoding the AAV rep and cap genes; and 3) an expression construct comprising the helper adenovirus genes required for the production of high titer virus. Following standard purification procedures, the viral particles are ready for use in experiments.

Before mice can be infused with the rAAV particles, a reporter system is established in the mouse livers. Hydrodynamic transfection is employed to deliver the luciferase reporter construct as well as an expression plasmid for hAAT to control for differences in transfection efficiencies from animal to animal. The mice are permitted to recover for several days in order to establish sufficient levels of reporter activity.

After luciferase reporter activity has been established in the livers, rAAV particles are infused into normal C57Bl/6 mice either through portal vein or tail vein injection. rAAV particles bearing the expression construct of an unrelated shRNA are used as a negative control. Initially, the mice are infused with relatively high doses ($2 \times 10^{12}$ vector genomes (vg)) which are reduced in follow-up experiments performed to generate dose-response curves. After seven to ten days, the mice are sacrificed, the livers harvested and samples of serum collected. The relative levels of hepatic luciferase activity and RNA are determined from the isolated livers utilizing the luciferase assay and QPCR procedures previously described. Additionally, the efficiency of transduction is assessed by measurement of the marker protein in serial slices of the hepatic tissues.

Results from the experiment may be wide ranging. It has been estimated that hydrodynamic transfection procedures may result in the transfection of 5-40% of hepatocytes. Transduction of liver cells by AAV-2 delivery procedures have been shown to result in 5-10% transduction efficiencies. Although AAV may preferentially transduce the same pool of hepatocytes that were transfected by the initial tail vein injection procedure, it is possible that the subsets of cells that each technique affects are non-overlapping. If the former occurs, a reduction in luciferase activity relative to mice transduced with an unrelated shRNA species is seen. If the latter occurs, then no decrease in luciferase activity is seen.

Figure 9:
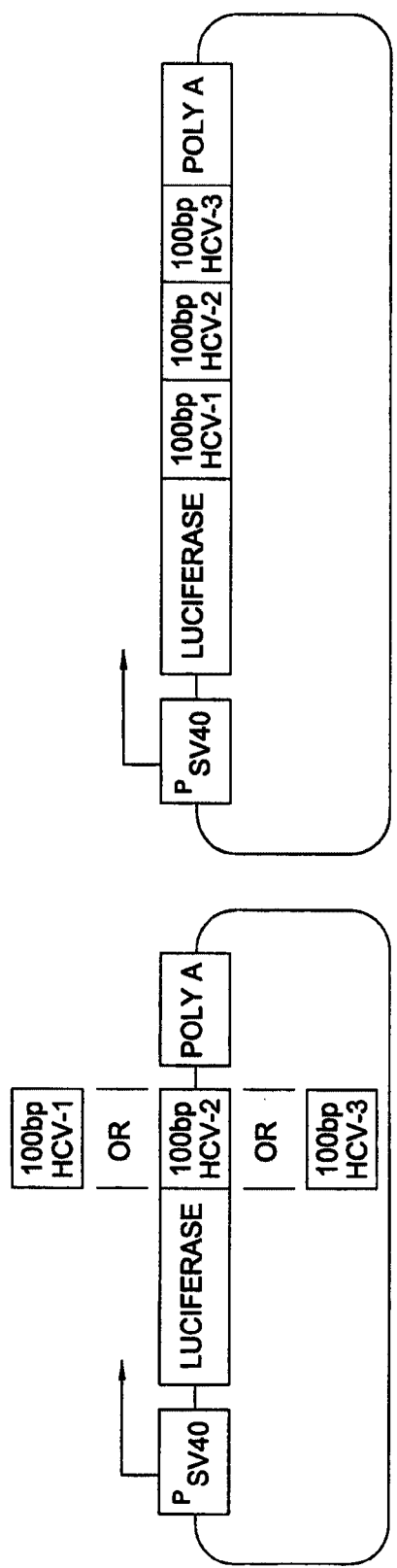
FIG. 9 is a schematic of two luciferase-HCV fusion reporter plasmids useful for testing RNAi agents. The construct on the left comprises one 100 by HCV sequence fused to a luciferase gene; while the construct on the right comprises 3 different 100 bp HCV sequences fused to a luciferase gene. RNAi agents targeting a sequence contained within the 100 bp region will, if effective, degrade the HCV-luciferase transcription product, thus decreasing (perhaps eliminating) luciferase expression.

It must be verified that AAV particles delivered by the triple expression construct inhibit the luciferase-HCV fusion reporter in vitro. Permissive tissue culture cells are transfected with one of the reporter constructs detailed in FIG. 9. In addition, each co-transfection mixture is supplemented with a plasmid coding for hAAT. Following 48 hours of incubation, cells are dosed with infectious particles harboring the triple promoter shRNA expression plasmid against HCV. AAV particles containing a triple promoter construct expressing three unrelated shRNA species serve as the negative control. Measurement of luciferase activity is used to verify that the AAV-delivered shRNA are highly functional.

Example 2

Modifications to Enhance Efficiency of AAV Transduction of Liver Tissues

Although it has been demonstrated that AAV-based vectors can deliver desired sequences to hepatocytes, the relative level of transduction that occurs within those tissues has traditionally been rather poor. For current clinical hemophilia studies which employ AAV-2 to deliver and express blood factor IX, this is not a significant issue. For treatment of hemophilia, it is critical only to replenish levels of secreted protein to therapeutic levels. Such replenishment may occur from a small number of transduced cells able to express significant levels of the desired protein. However, because the mechanism of RNAi action is intracellular and the effect is not transmitted directly from cell to cell, the transduction efficiency must be increased in order for AAV expressing shRNA to be utilized as a therapeutic.

McCarty et al. were able to generate a self complementary AAV vector (scAAV) that has both a plus and a minus strand of the same expression cassette within its capsid *Gene Ther.* 8: 1248-1254 (2001)). This was achieved by mutating the 5' ITR and leaving the 3' ITR intact. By mutating or deleting the terminal resolution site other non-essential AAV sequences, thus eliminating possible recombination by wild type AAV and this construct, a DNA template is created where replication starts at the 3' ITR. Once the replication machinery reaches the 5' ITR, no resolution takes place and replication continues to the 3' ITR. The resulting product has both a plus and complementary minus strand, yet is efficiently packaged. Employing the scAAV vectors, transduction of liver cells was increased to 30% of the total hepatocytes (Fu, et al. *Molec Therapy.* 8(6):911-7. (2003)). When delivered intercisternally, more than 50% of the Purkinje cells in the cerebellum were transduced by the scAAV particles. Thomas et al. showed that self-complementary vectors could produce 50-fold higher luciferase transgene expression levels in mouse livers than their corresponding single-stranded AAV counterparts when infused into mouse livers at equivalent doses (Thomas, et al., *J. Virol.* (in press)). Though dropping slightly, the relative difference of expression between the vectors persisted at 20-fold nearly one year after injection.

Similar strategies are employed herein. Because of the size limitations associated with packaging the rAAV multiple-promoter RNAi expression construct, the amount of space that may be utilized for delivery of therapeutic sequences—already quite small by comparison to other viral delivery systems—is halved by the use of scAAV. Thus, instead of being able to package 4500 nucleotides, the limit is lowered to 2250 nucleotides. Regardless, the size of the multiple-promoter RNAi expression cassette allows such construction. A graphic of the major elements within the scAAV is shown in FIG. 6.

Other modifications of AAV-delivery systems also have been used to dramatically enhance transduction efficiencies, including the production of pseudotyped viral particles by packaging rAAV-2 vector genomes with the Cap protein from other serotypes. Because they have been among the best characterized of all of the serotypes, the Cap proteins from AAV-1 through AAV-6 are used most commonly to pseudotype the AAV-2 vectors. Even with the advantages gained by these employing pseudotyping strategies, the threshold of transduction efficiency of hepatocytes may be increased only to 15% of the total population. However, dozens of other serotypes of AAV have been isolated and identified, but have not been characterized to any appreciable degree. For example, one of these is AAV-8, which was isolated originally from the heart tissue of a rhesus monkey. In an effort to determine effects novel cap proteins on transduction, pseudotyped virus in which the single stranded AAV-2 genome was pseudotyped with AAV-8 cap was created. The vectors carried the LacZ gene to assess the relative efficiency of transduction of mouse livers after infusion with increasing doses of infectious particles. A summary of the results (Thomas, et al. *J. Virol.* 78(6):3110-22. (2004)) is shown below in Table 1:

TABLE 1

AAV-2/2 and AAV-2/8 Dose Response (% beta-gal positive hepatocytes)

| Vector | DOSE (v.g./Mouse) | | | | |
|---|---|---|---|---|---|
| | $5 \times 10^{10}$ | $3 \times 10^{10}$ | $1.8 \times 10^{11}$ | $3.9 \times 10^{12}$ | $7.2 \times 10^{12}$ |
| AAV-2/2 LacZ | 0.6 ± 0.4% | 3.0 ± 0.5% | 8.1 ± 1.0% | 8.9 ± 1.0% | NA |
| AAV-2/8 LacZ | 8.1 ± 1.8% | 14.9 ± 3.4% | 65.8 ± 9.1% | NA | 97.4 ± 0.3% |

As the dose of infused control AAV-2/2 particles is increased, there is a modest increase in transduction of hepatocytes; however, the upper threshold of transduction remains entrenched near the 10% limit. Surprisingly, pseudotyped AAV-2/8 particles transduced 8% of hepatocytes at the lowest dose of particles administered; doses that were 30-80 fold less than their AAV-2/2 counterparts. Additionally, the dose-dependent increase in transduction efficiency for AAV-2/8 surpassed the transduction efficiency for AAV-2/2 to greater than 97% at the highest dose. Transduction efficiencies within this range enable to efficient delivery of RNAi to cells within tissues.

Similar modifications of AAV are engineered into the rAAV RNAi expression constructs. Following incorporation of these simple modifications, stocks of virus are generated for testing in the mouse model system. The following rAAV RNAi experimental virus stocks are tested: single-strand AAV-2/2; single-strand AAV-2/8; self-complementary AAV-2/2; and self-complementary AAV-2/8.

Corresponding viral particles that harbor rAAV vectors expressing unrelated shRNA sequences are produced and used as negative controls. Large decreases in relative levels of luciferase activity correlate with increases in transduction efficiency.

Example 3A

Selection and Testing of RNAi Agents Against a Luciferase-HCV Fusion Plasmid The selection of shRNAs useful as therapeutics against HCV is not a straight-forward proposition. In addition to the problem of the generation of escape mutants, the high mutation rate leads to a rather large degree of sequence divergence within a population of infected individuals harboring the virus, with genotypes differing by as much as 31-34% in their nucleotide sequences. Subtypes (species within a given genotype) may differ by 20-23% based on full-length genomic sequence comparisons. Thus, regions of the viral genome with a high degree of conservation preferably are identified and chosen to ensure the broadest therapeutic applicability. As an example of how sequences are aligned and therapeutically relevant regions selected, 30 full-length sequences corresponding to HCV genotype 1b virus were retrieved from public databases and aligned using the Jotun Hein Method and MegAlign analysis software (DNASTAR). Regions with a high degree of conservation were identified, such as a region in the 5' UTR (nucleotides 75-112).

To select candidate sequences, an alignment of all published independent full-length or near-full-length HCV sequences was performed; currently there are over 200 such sequences available representing all known genotypes. Several candidate regions for selection and development of RNAi therapeutics currently exist and it is well-documented that the 5' and 3' UTR regions are amongst the most highly conserved regions in the HCV genome. Despite perception that these non-coding sequences may not represent optimal sequences to target due to the potential for steric hindrance with the cellular translation complex proteins or regulatory proteins, Yokota et al. have already identified a highly functional RNAi targeting the 5' UTR in a replicon system (*EMBO Rep.* 4(6): 602-608 (2003)). Although it would be beneficial to identify several regions of absolute identity within individual stretches of 21 nucleotides (the corresponding size of the targeting sequences in a shRNA species), analysis to date demonstrates that such a degree of conservation does not occur within the various subtypes of a specified genotype, let alone across all genotypes. Thus, selection may include segments of the genome in which greater than 80% of the regions maintain absolute conservation. In a final construction of a preclinical candidate, the expression of three independent shRNAs compensates for the sequence variability, allowing for a combination therapy contained within a single delivery vehicle.

Alternatively, if conserved regions that meet the selection criterion in an analysis of all HCV genotypes are not identified, sequence analysis may be restricted to genotype 1 (1a and 1b), which accounts for nearly three quarters of the infected population with the United States and, with the exception of Africa, is the predominate genotype throughout the world. In addition, the most current effective anti-HCV therapy, a combination of pegylated interferon with Ribavirin (a guanosine analogue), is rather inefficient against genotype 1, but highly efficient against the other genotypes. Thus, the greatest need for an alternative therapy exists in the largest patient population. As sequence alignments only reveal homology, other selection criteria, such as relative GC content and the lack of cross specificity when queried against sequence databases, is applied when selecting the final RNAi agents to be tested.

For example, for one experiment, alignment was performed for multiple sequences from HCV subtypes 1a and 1b. A few conserved regions were identified as being long enough from which to select RNAi agents for testing (>19 nucleotides). The 5'UTR and 3'UTR regions were the most conserved regions. Since the regions of homology that were identified were quite long, alignment also was performed between different genotypes. Combining the two alignments allowed selection of universally conserved regions. Some regions, such as a long stretch of A' s or U' s, or of G' s and C' s were removed from consideration because they are not amenable to targeting with RNAi agents, leaving "qualified" regions for further selection. Only one universally conserved region was identified in the whole coding region (the open reading frame) for all of the genotypes of HCV considered; therefore, the sequences selected for targets in most cases were those that are conserved in subtypes 1a and 1b.

Once "qualified" regions were identified, individual RNAi sequences were selected applying the criterion that the 5' end of the antisense strand in the RNAi agent should possess a lower free energy than the 3' end. "Neighbor pair free energy" rules were applied to calculate free energy for the terminal five nucleotides on both the 5' and 3' ends of all potential RNAi agents selected thus far. As a result, a total of 30 potential RNAi agents were identified: ten in the 5'UTR (5'-n), twelve in the Open Reading Frame ORF (C-n), and eight in the 3'UTR (3'-n) (see Table 2). The relative locations of these RNAi target sites on the HCV genome are shown in FIG. 8A.

TABLE 2

RNAi Sequences

| RNAi agent | RNAi sequence ‡ | SEQ ID NO. | Luc Reporter Plasmid | HCV Location |
|---|---|---|---|---|
| 5'-1 | gCTGTGAGGAACTACTGTCT | SEQ ID NO. 1 | 20 | IRES 43-62 |
| 5'-2 | GTCTAGCCATGGCGTTAGT | SEQ ID NO. 2 | — | IRES 77-95 |
| 5'-3 | GGAGAGCCATAGTGGTCTG | SEQ ID NO. 3 | 16, 20 | IRES 131-149 |
| 5'-4 | GCGGAACCGGTGAGTACAC | SEQ ID NO. 4 | 16 | IRES 150-168 |
| 5'-5 | GTCTGCGGAACCGGTGAGTA | SEQ ID NO. 5 | 16 | IRES 146-165 |
| 5'-6 | GCGAAAGGCCTTGTGGTACT | SEQ ID NO. 6 | 16, 17 | IRES 270-289 |
| 5'-7 | GATAGGGTGCTTGCGAGTG | SEQ ID NO. 7 | 16 | IRES 295-313 |
| 5'-8 | GAGGTCTCGTAGACCGTGCA | SEQ ID NO. 8 | 16, 17 | IRES 319-338 |
| 5'-9 | gCTTGTGGTACTGCCTGATA | SEQ ID NO. 9 | — | IRES 279-298 |
| 5'-10 | gCTGCCTGATAGGGTGCTTGS | SEQ ID NO. 10 | 17 | IRES 289-307 |
| C-1 | AGATCGTTGGTGGAGTTTA | SEQ ID NO. 11 | — | Core 427-445 |
| C-2 | gTTGGGTAAGGTCATCGATA | SEQ ID NO. 12 | — | Core 696-714 |
| C-3 | GCCGACCTCATGGGGTACAT | SEQ ID NO. 13 | 18 | Core 732-752 |
| C-4 | GGTTGCTCTTTCTCTATCT | SEQ ID NO. 14 | — | Core 852-870 |
| C-5 | GGGATATGATGATGAACTG | SEQ ID NO. 15 | — | NS1 1300-1318 |
| C-6 | GGATGAACCGGCTAATAGC | SEQ ID NO. 16 | — | NS4B 6085-6113 |
| C-7 | GGAGATGGGCGGCAACATC | SEQ ID NO. 17 | — | NS5A 7046-7064 |
| C-8 | GTCTTCACGGAGGCTATGA | SEQ ID NO. 18 | — | NS5B 8610-8629 |
| C-9 | GTCAACTCCTGGCTAGGCAA | SEQ ID NO. 19 | — | NS5B 8811-8830 |
| C-10 | gTCCACAGTTACTCTCCAGG | SEQ ID NO. 20 | — | NS5B 9019-9037 |
| C-11 | gCCTCTTCAACTGGGCAGTA | SEQ ID NO. 21 | — | NS5B 9170-9188 |
| C-12 | AGCTTAAACTCACTCCAAT | SEQ ID NO. 22 | — | NS5B 9196-9214 |
| 3'-1 | GCTCCATCTTAGCCCTAGT | SEQ ID NO. 23 | 19 | 5-23* |
| 3'-2 | gTCCATCTTAGCCCTAGTCA | SEQ ID NO. 24 | 19 | 7-25* |
| 3'-3 | GTCACGGCTAGCTGTGAAA | SEQ ID NO. 25 | 19 | 22-40* |
| 3'-4 | ACGGCTAGCTGTGAAAGGT | SEQ ID NO. 26 | 19 | 25-43* |
| 3'-5 | GCTGTGAAAGGTCCGTGAG | SEQ ID NO. 27 | 19 | 32-50* |
| 3'-6 | GGTCCGTGAGCCGCATGAC | SEQ ID NO. 28 | — | 41-59*^ |
| 3'-7 | GCCGCATGACTGCAGAGAGT | SEQ ID NO. 29 | — | 50-69*^ |
| 3'-8 | ACTGGCCTCTCTGCAGATCA | SEQ ID NO. 30 | — | 76-95*^ |

‡Lower case letters indicate sequences not corresponding to either the HCV fusion replicon or the HCV genome

TABLE 3

Luciferase-HCV fusion plasmids

| Luciferase-HCV fusion Plasmid | HCV Target Region |
|---|---|
| #20 | 5'1-through-5'5 |
| #16 | 5'3-through-5'10 |
| #17 | 5'6-through-5'10 |
| #12 | 5'7-through-5'10, Coding-1 |
| #18 | Coding-3 |
| #19 | 3'1-through-3'8 |
| C2 & 4 | Coding-2, Coding-4 |
| C5 | Coding-5 |
| C6 | Coding-6 |
| C7 | Coding-7 |
| C8 | Coding-8 |
| C9 | Coding-9 |
| C10 | Coding-10 |
| C11 & 12 | Coding-11, Coding-12 |
| C6-C9-C12-3'1 | Coding-6, Coding-9, Coding-12, 3'1 |

To test the efficacy of the RNAi sequences selected, RNAi agents were delivered directly to cultured cells along with a Luciferase-HCV fusion plasmid. A schematic representation of the Luciferase-HCV fusion plasmid used in these experiments is shown on the left panel of FIG. 9. It comprises a gene sequence coding for firefly luciferase protein fused to 100 bp stretches of nucleic acid, corresponding to HCV target sequences—the regions of HCV from which the RNAi agents were derived. RNAi agents directed against a sequence within the 100 bp region will, if effective, degrade the luciferase-HCV transcription product, thus decreasing or eliminating luciferase expression. Table 3 lists some of the corresponding Luciferase-HCV fusion plasmids and the HCV target regions used.

Pre-synthesized siRNA agents were obtained from Dharmacon, Inc. (Lafayette, Colo.). Huh7 cells were seeded in 12-well plates at $9.5 \times 10^5$ cells per well 24 hours before the time of transfection. At the time of transfection the cells were ~30-40% confluent. 350 µl OptiMEM (Invitrogen Inc.) media was mixed with 15 µl NovaFECTOR (VennNova, Pompano Beach, Fla.), and incubated for 1 hour at room temperature. 50 µl OptiMEM was mixed with 0.05n pRL-SV40 (Promega), 0.45 µg of the Luc-HCV reporter plasmid, and 2 µl of the appropriate RNAi agent (20 µM stock). NovaFECTOR solution was added to the DNA/RNAi mixture, and incubated for 15 minutes at room temperature. Cells were rinsed once with OptiMEM and transfected with 4000 of the NovaFECTOR/DNA/RNAi mixture. Cells were then incubated at 37° C. in 5% $CO_2$ atmosphere for 1.5 hours. One milliliter of complete medium was added to each well, and incubation was continued for an additional 2.5 hours, at which time the medium was replaced with a fresh complete medium. Further incubation was continued for two days.

After two days, the medium was aspirated and the cells were lysed and measured for luciferase expression according to the manufacturer's dual luciferase protocol (Promega, Madison, Wis.). Percent of inhibition was calculated based on normalized luciferase relative light units (RLUs) versus cells transfected with a non-specific RNAi species with no known endogenous target. The data was normalized for differences in transfection efficiency based on expression of *Renilla* luciferase activity from a pRL-SV40 plasmid that was co-transfected with the Luciferase-HCV fusion plasmids.

Figure 12:
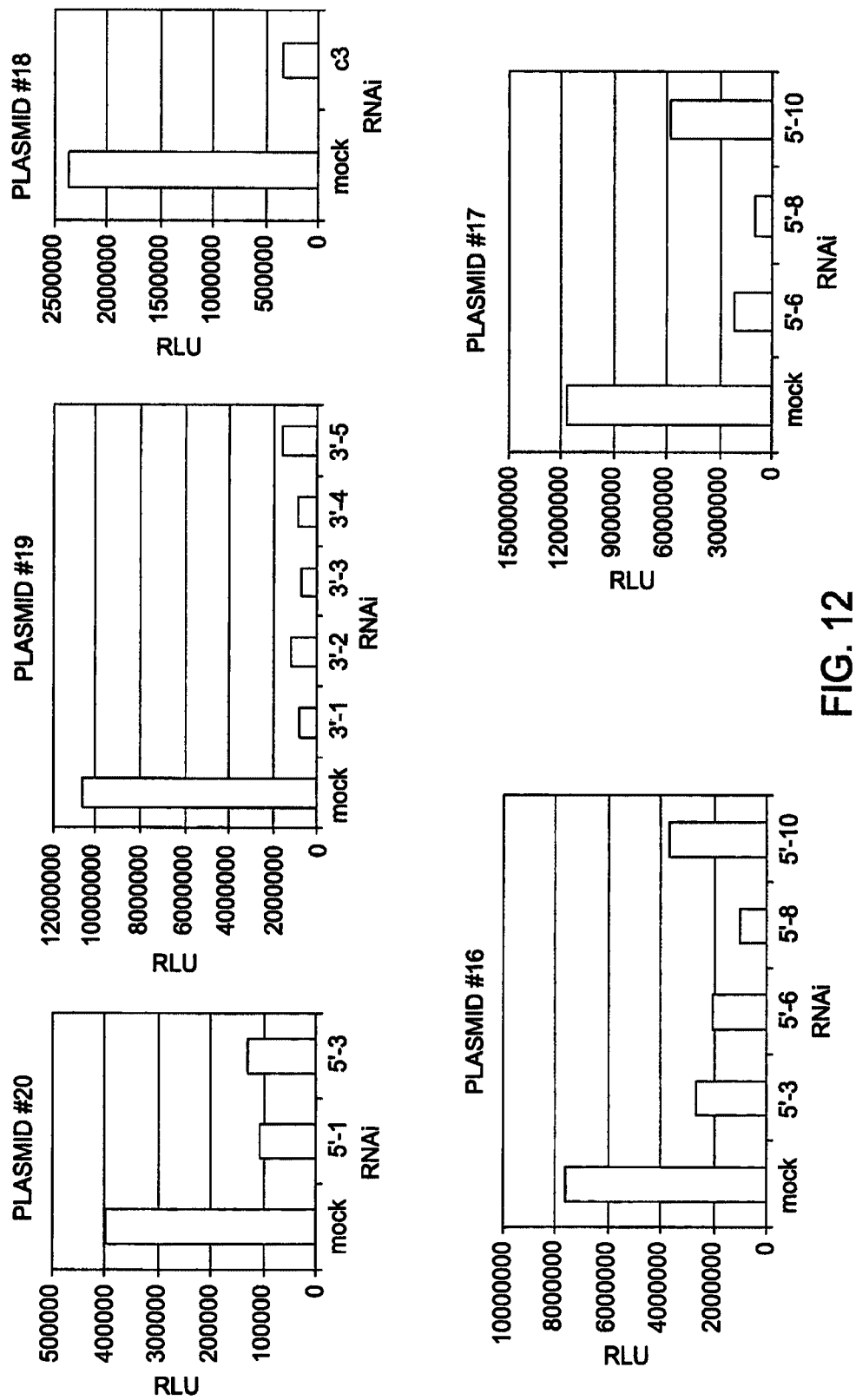
FIG. 12 shows the results of inhibition of luciferase expression measured in relative light units (RLU) by different RNAi agents targeting five different 100 bp regions of HCV.
Figure 13:
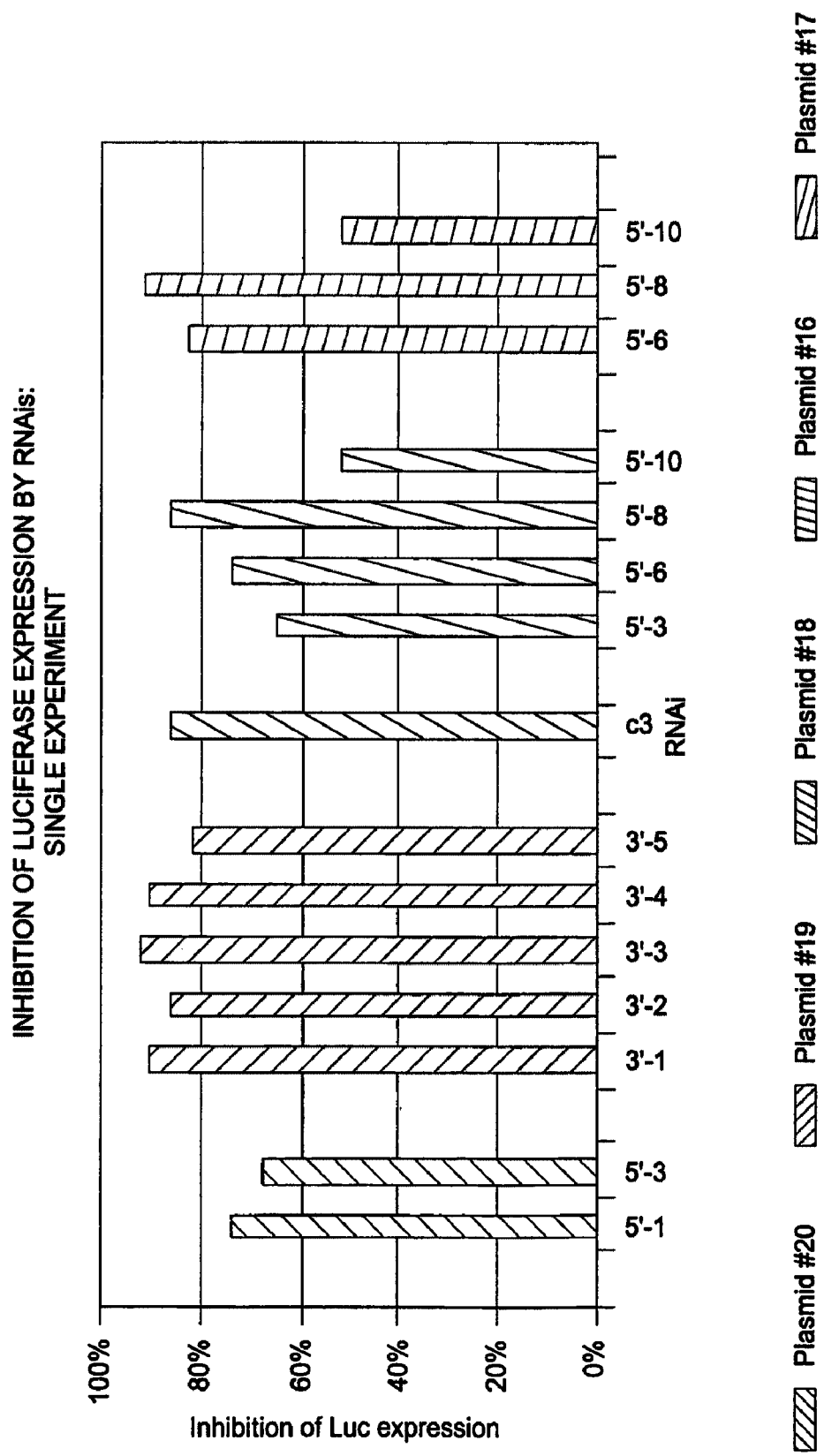
FIG. 13 shows the results of inhibition of luciferase expression by different RNAi agents expressed as a percent inhibition value.

FIG. 12 shows the results of inhibition of luciferase expression measured in relative light units by different RNAi agents targeting five different 100 bp regions of HCV; and FIG. 13 shows the results of inhibition of luciferase expression where the data of FIG. 12 is expressed as a percent value. In looking at these results, note that at least 50% inhibition was achieved with all selected RNAi agents, and over half of the plasmids inhibited luciferase expression by greater than 80%.

Figure 14:
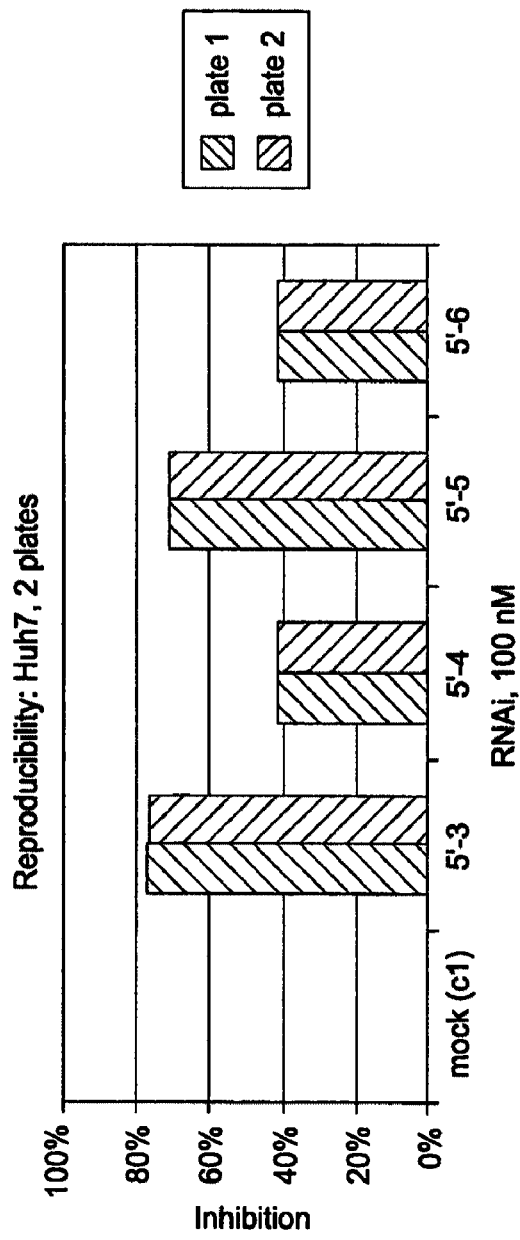
FIG. 14 shows the reproducibility of the results of experiments performed testing four different RNAi agents targeting various segments of a 100 bp sequence from the 5' region of HCV.

FIG. 14 shows the reproducibility of the results of experiments performed testing four different RNAi agents (5'-1,5'-2,5'-3, and 5'-4) targeting various segments of a 100 bp sequence in the 5' region of HCV. Note that reproducibility was excellent for each agent tested.

Figure 15:
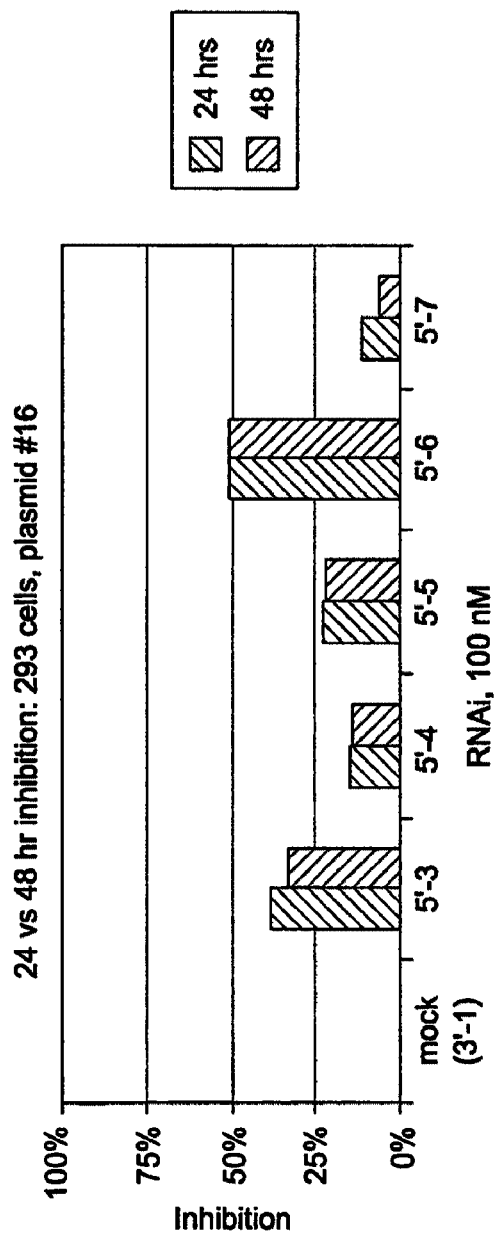
FIG. 15 shows the change in percent inhibition of luciferase expression 24 hours post transfection and 48 hours post transfection for five different RNAi agents targeting various segments of a 100 bp sequence in the 5' region of HCV.

FIG. 15 shows the change in percent inhibition of luciferase expression 24 and 48 hours post transfection for five different RNAi agents (5'-3,5'-4,5'-5,5'-6 and 5'-7) targeting various segments of a 100 bp sequence in the 5' region of HCV.

Figure 16:
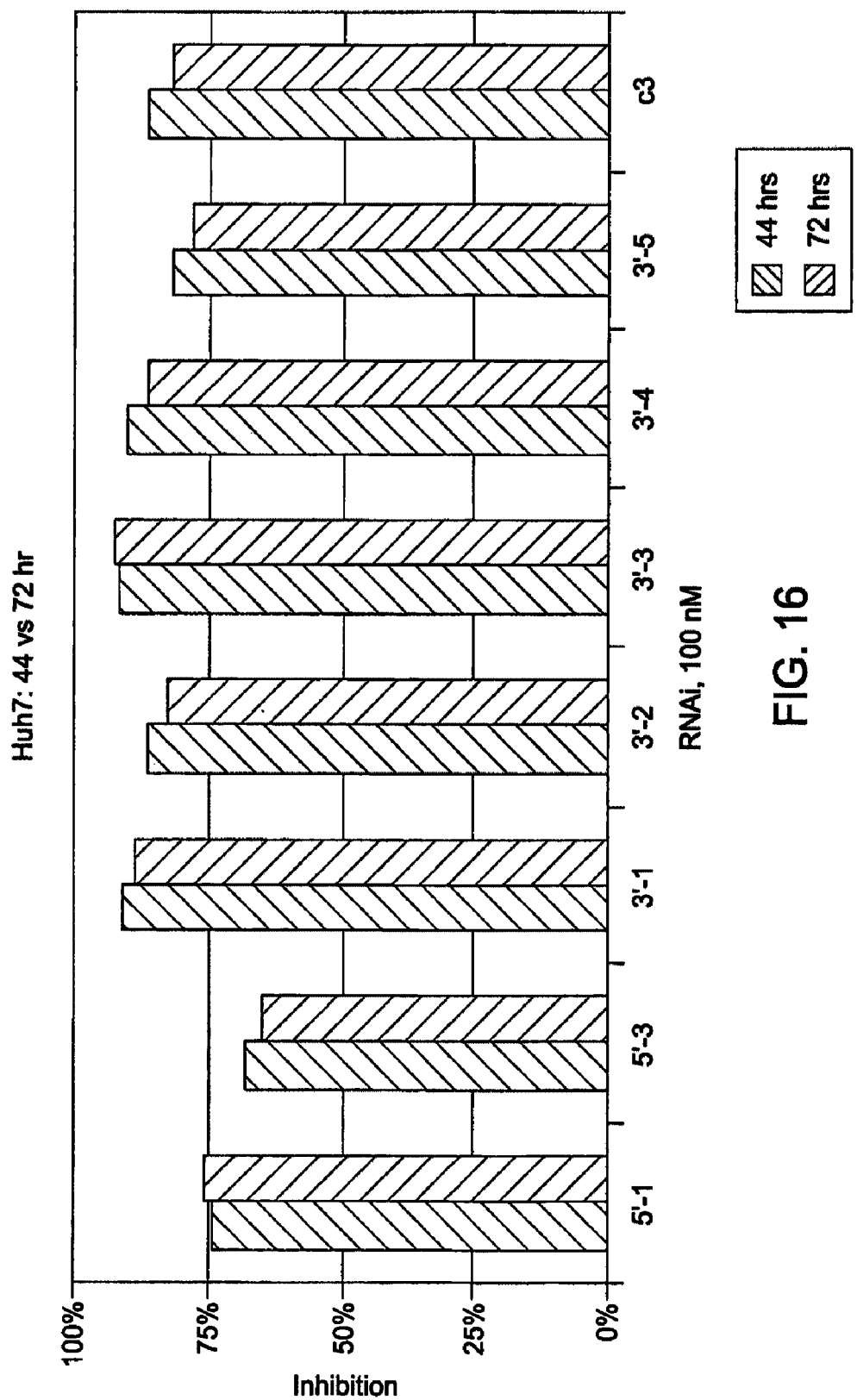
FIG. 16 shows the change in percent inhibition of luciferase expression 44 hours post transfection and 72 hours post transfection for two different RNAi agents targeting various segments of a 100 bp sequence in the 5' region of HCV, five different RNAi agents targeting various segments of a 100 bp sequence in the 3' region of HCV, and one RNAi agent targeting a segment of a 100 bp sequence in the open reading frame region of HCV.
Figure 17A:
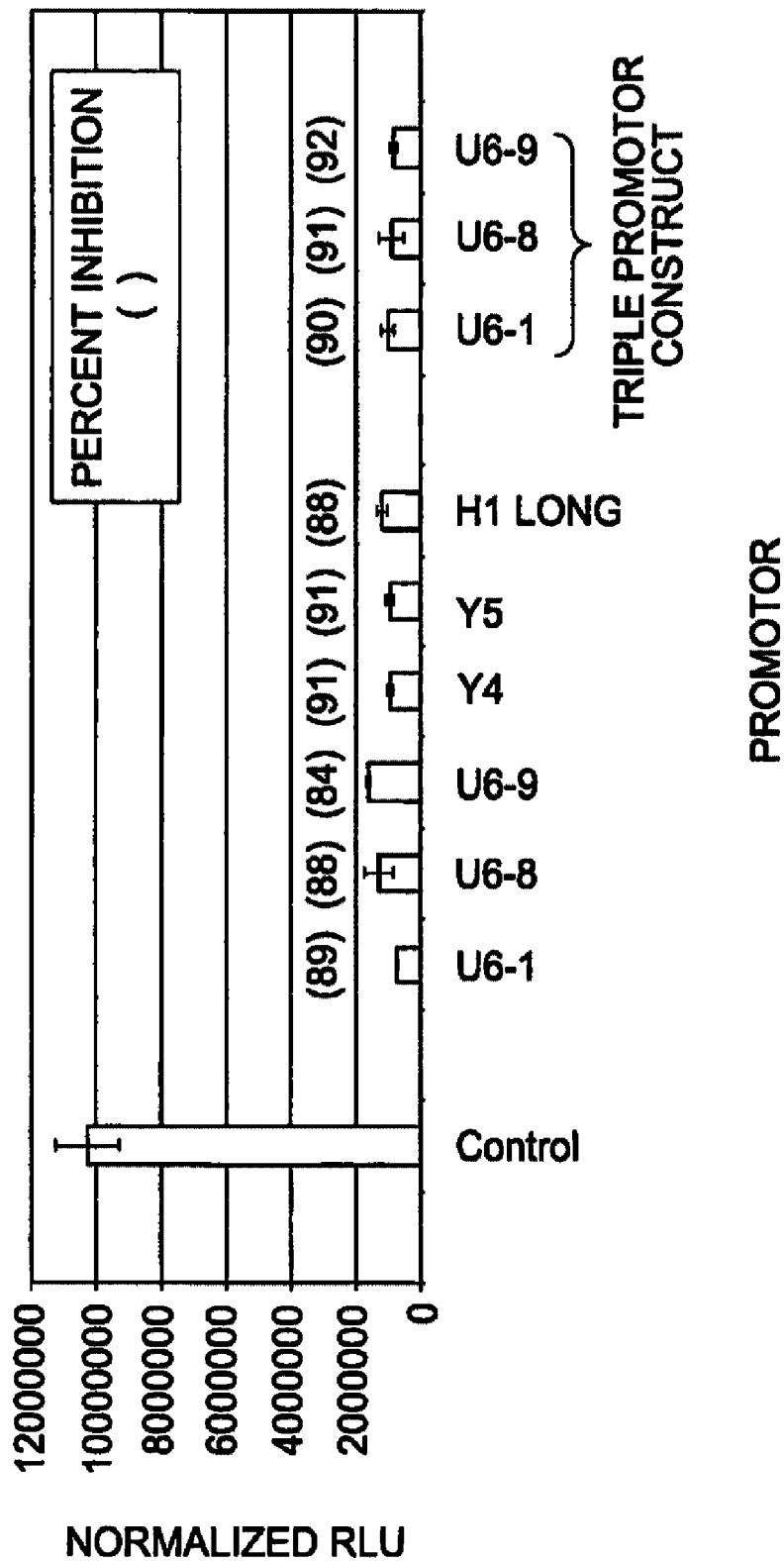
FIGS. 17A and 17B show data assessing the strength of three Pol III promoters. An shRNA sequence specific to firefly luciferase mRNA (McCaffrey at al., 2002) was inserted under control of indicated Pol III promoter. Resulting plasmid DNA was co-transfected together with a luciferase reporter plasmid either in Huh7 cells (FIG. 17A) or 293 cells (FIG. 17B). Luciferase levels were measured 72 hrs post transfection. In triple-promoter constructs from FIG. 3B (right three constructs on each panel) the promoter driving shRNA is indicated.
Figure 17B:
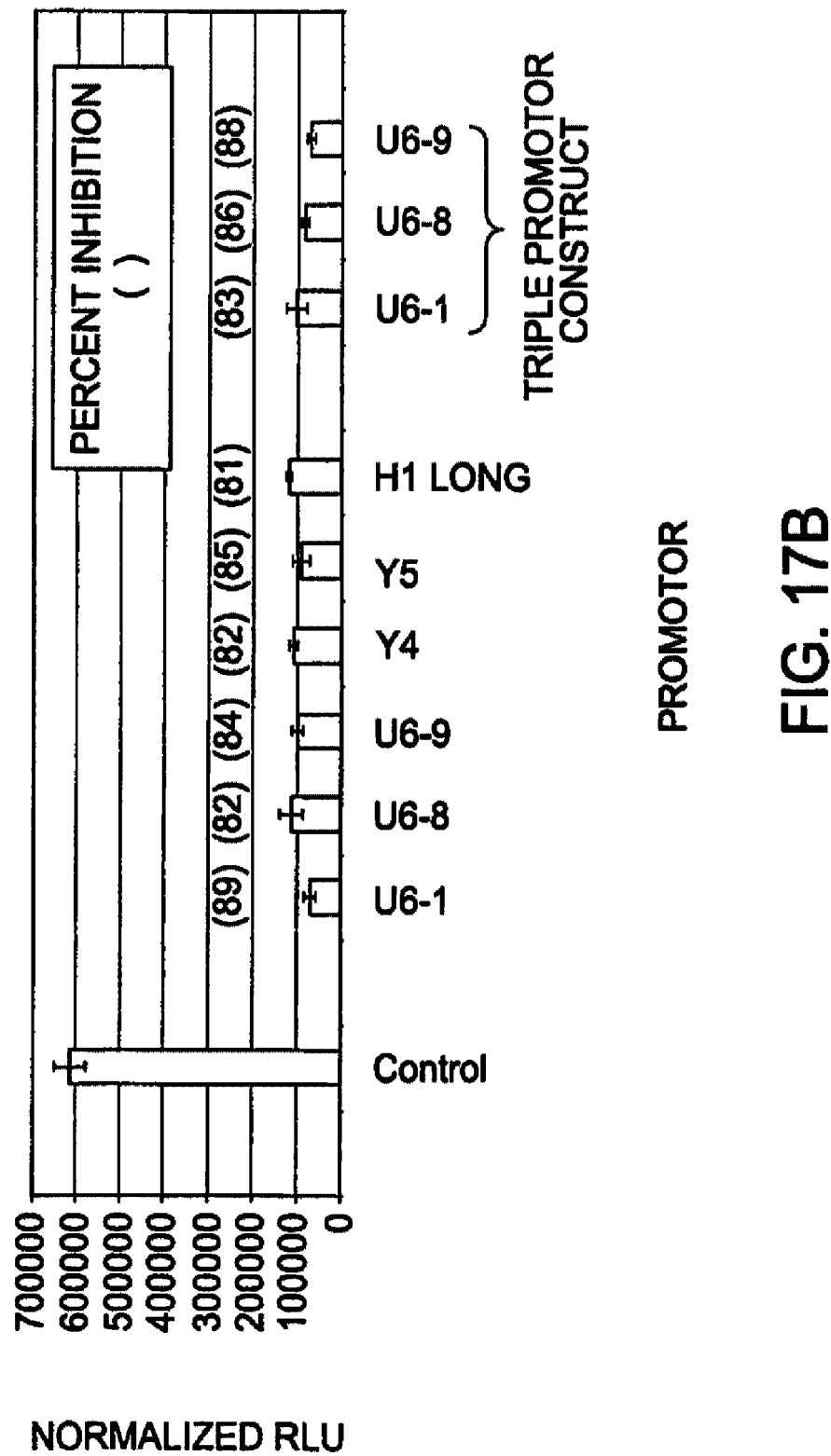

FIG. 16 shows the change in percent inhibition of luciferase expression 44 and 72 hours post transfection for two different RNAi agents targeting various segments of a 100 bp sequence in the 5' region of HCV (5'-1 and 5'-3), five different RNAi agents targeting various segments of a 100 bp sequence in the 3' region of HCV (3'-1,3'-2,3'-3,3'-4 and 3'-5), and one RNAi agent targeting a segment of a 100 bp sequence in the open reading frame region of HCV (C-3). Inhibition is maintained at 72 hours post infection to within about 10 percent of 44 hour levels.

Figure 18:
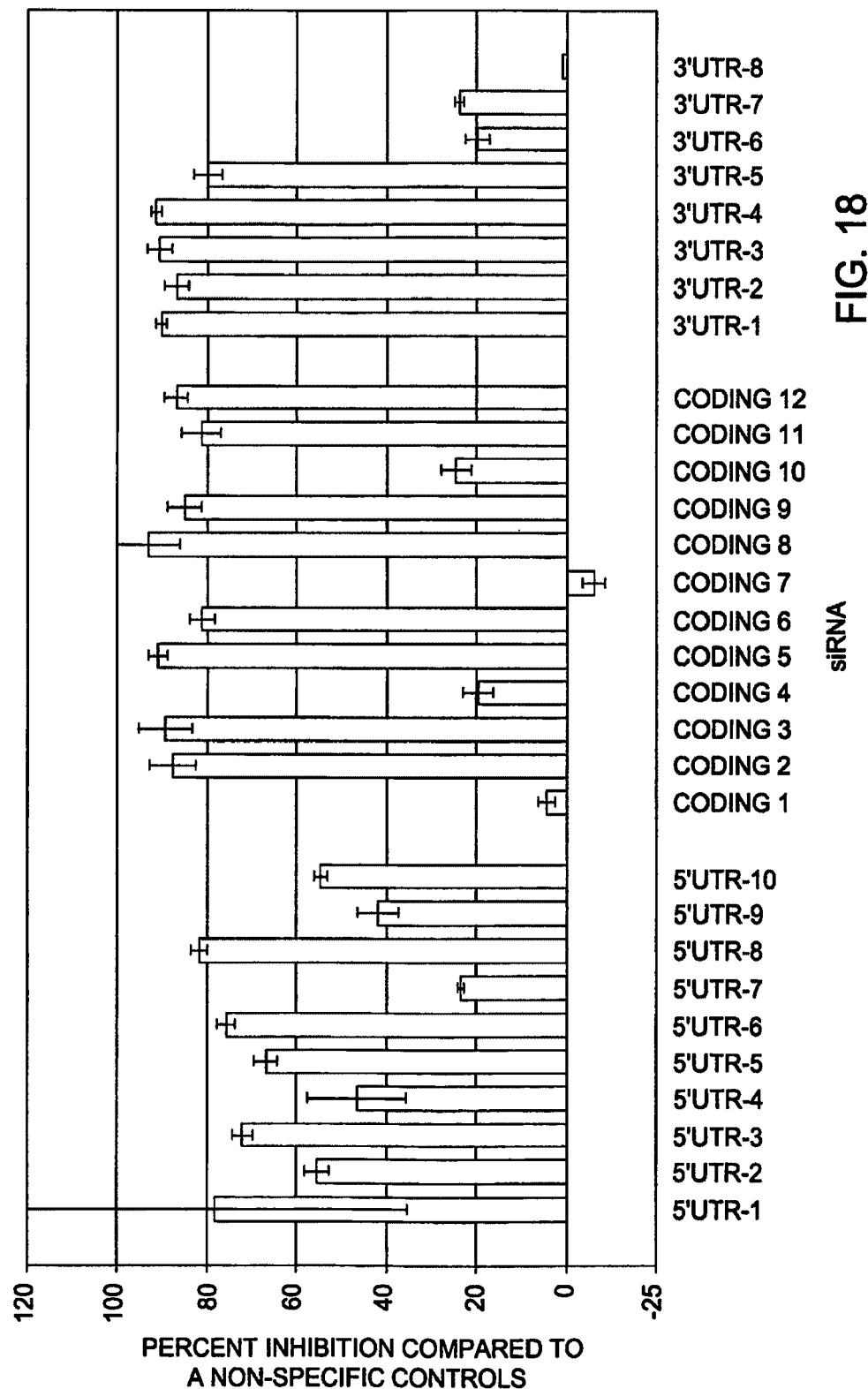
FIG. 18 shows the inhibition of luciferase expression with different siRNA agents in luciferase-HCV fusion reporter plasmid assay. The luciferase-HCV reporter plasmid was co-transfected with each siRNA agent into Huh7 cells, and luciferase activity was measured 48 hrs later.

FIG. 18 shows the luciferase inhibition resulting from treatment with a wide variety of RNAi agents targeted to various regions in the HCV genome in a luciferase-HCV fusion plasmid. Luciferase activity is measured 48 hours after co-transfection with an RNAi agent into Huh7 cells. It can be seen from this data that RNAi agents can effectively target all regions of the HCV genome and result in strong inhibition of luciferase reporter signal.

Example 3B

Selection and Testing of RNAi Agents Against Luciferase-HCV Replicon System

Although many of the individual steps of HCV replication are understood, until recently there was no tissue culture system that propagated the viral life cycle, making studies of the virus difficult. However, an in vitro replicon system has been developed (see, e.g., U.S. Pat. Nos. 5,585,258; 6,472,180; and 6,127,116 to Rice, et al.). A replicon is an autonomously replicating portion of HCV genomic RNA that may contains a marker gene for selection and verification of replication. HCV-RNA constructs are transfected into cell lines that are amenable to support continuous propagation. Following the steps of the infectious cycle, the RNA is translated by the cellular machinery and produces both the appropriate viral proteins required for replication of the genome, as well as the selectable marker, if present. Full-length and sub-genomic replicons have been generated and shown to be functional, although only the non-structural proteins are obligate. The autonomously replicating properties of the RNA remain independent of expression of the structural genes. Even when present in replicons expressing the full length HCV genome, the core and envelope proteins fail to effectively package the genome into infectious particles—resulting in the loss of a model system to study the packaging, egress and re-entry steps of the virus. Regardless, the replicon is able to recreate a portion of the biology and mechanisms utilized by HCV.

In addition to or as an alternative to using luciferase or other such reporters, the level of replicon activity may measured by a variety of other methods. The inhibition of HCV replication may be assessed by observation of the relative levels of non-structural proteins by immunofluorescence microscopy utilizing a panel of commercially available HCV-specific monoclonal antibodies. Alternatively or in addition, Q-PCR may be used to measure the relative level of HCV genomic RNA from each transfected condition.

Figure 8B:
Figure 8C:
Figure 19:
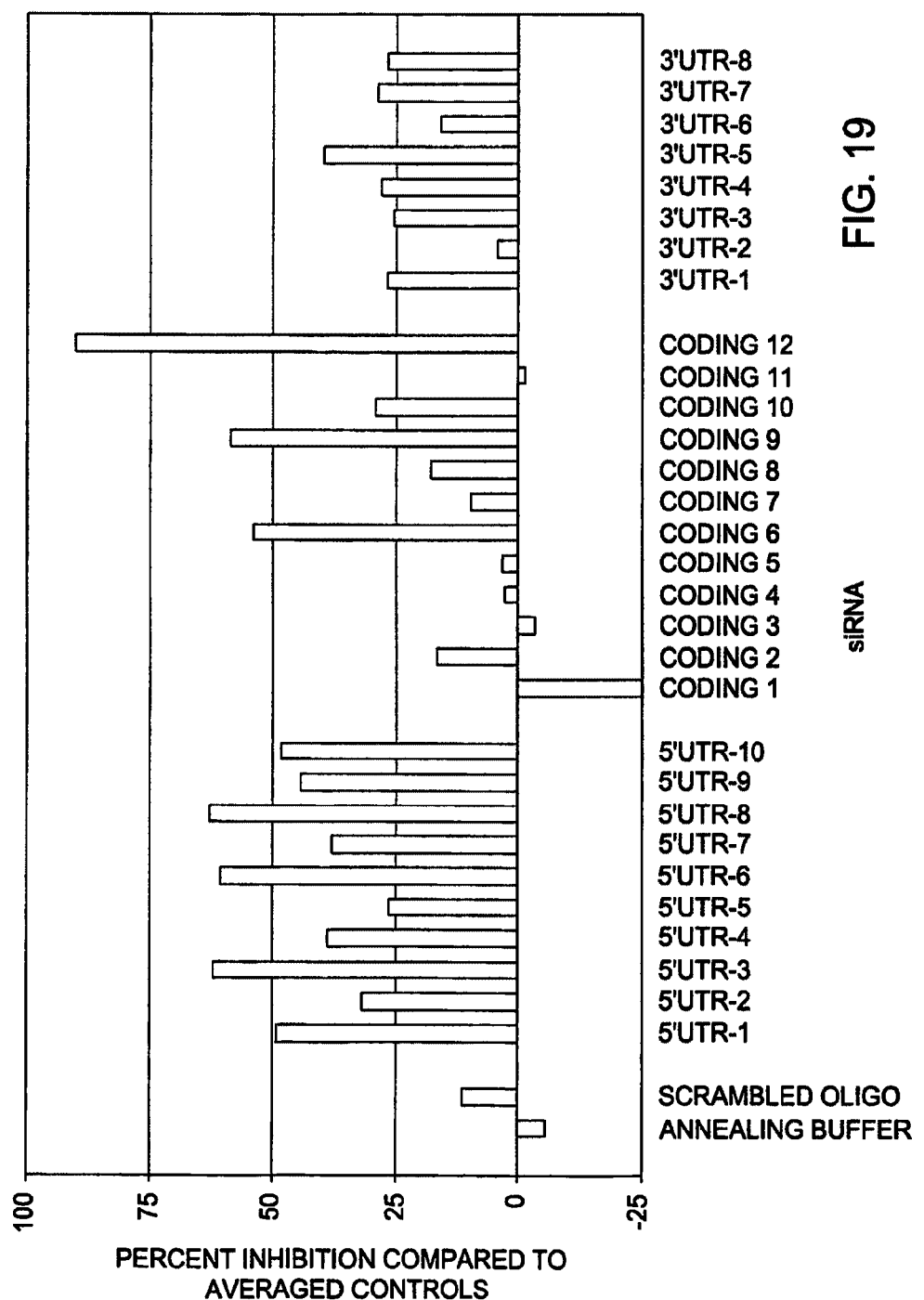
FIG. 19 shows the activity of selected siRNA agents against a subgenomic Luciferase-HCV fusion replicon. Tested siRNA agents were transfected into 29Σ cells together with a trace amount of pGL3Control DNA (as a control for transfection efficiency). Both renilla and firefly luciferase levels were measured 48 hours later.

The ability of siRNA agents to inhibit replication of the genomic RNA was tested by measurement of renilla luciferase expression in a cell line transformed by the Luciferase-HCV fusion replicon. Five siRNAs could not be tested in the subgenomic replicon system due to an absence of the corresponding sequence and were included in the tests merely as nonspecific controls. Schematic diagrams of the Luciferase-HCV replicons are shown in FIGS. 8B and 8C. Cells were seeded in a 96-well plate; following 24 hour incubation, interferon alpha 2B (IFN), known to inhibit HCV replicon activity (Blight, et al. *Science*. 290: 1972-74 (2000)), was added into specified wells at a concentration of 100 units per ml. Following an additional 48 hours of incubation, the medium was discarded and a cell extract generated in situ and luciferase activity was measured. Luciferase activity corresponded precisely to the levels of luciferase-mRNA (data not shown). In testing RNAi agents, 291 cells containing the Luciferase-HCV replicon (shown in FIG. 8B) are transfected with RNAi agents targeting a variety of regions in the HCV genome. Cells are harvested after 48 hours, extracts generated and the relative level of luciferase activity assessed. FIG. 19 shows the results of luciferase inhibition by siRNA agents directed to various regions of the Luciferase-HCV replicon. RNAi agents directed at coding regions C-1 through C-5 do not have targets in the Luciferase-HCV replicon and serve as additional non-specific controls. Once again targets in all regions of the HCV genome can act as effective inhibition sites for siRNA agents.

Once several highly functional RNAi are selected and tested individually, they are then triple transfected into cells harboring the replicon system. One control consists of transfecting an equivalent number of unrelated RNAi species in parallel. The inhibitory activity of the triple transfections is compared to activity from a set of parallel plates that have been transfected with only one RNAi species.

Three RNAi agents are validated, and the coding sequences for each corresponding shRNA is generated from long, complementary self-annealing oligonucleotides and cloned into the individual sites of the triple promoter AAV vector. This construct is then packaged into viral particles according to the methods described herein utilizing the system that results in the highest transduction efficiency of liver tissues. The total length of each promoter/RNAi/terminator component of the triple promoter cassette is small (~400 nucleotides); linking three promoter/RNAi/terminator components together results in a sequence that is 1200-1300 nucleotides in length, far below the upper size limit of self-complementary AAV.

The inhibitory activity of these particles is tested on cell lines harboring the replicon. Generation of a triple promoter construct expressing three unrelated shRNA species serves as a negative control. The efficacy of the shRNA sequences is monitored by aforementioned analysis techniques.

Example 4

Development of a Triple Promoter Expression Construct

Construction of a triple promoter expression construct includes three independent promoter and terminator sequences that drive the expression of the individual shRNA species at comparable levels of abundance. Repetition of promoter elements may leave integrated expression cassettes susceptible to recombination events; thus, three distinct promoters and terminators are identified and validated. The synthesis of small nuclear RNAs and transfer RNAs is directed by RNA polymerase III (pol III) under the control of pol III-specific promoters. Because of the relatively high abundance of transcripts directed by these regulatory elements, pol III promoters, including those derived from the U6 and H1 genes, have been used to drive the expression of shRNA (see, e.g., Domitrovich and Kunkel. *Nucl. Acids Res*. 31(9): 2344-52 (2003); Boden, et al. *Nucl. Acids Res*. 31(17): 5033-38 (2003a); and Kawasaki, et al. *Nucleic Acids Res*. 31(2): 700-7 (2003)).

Figure 7:
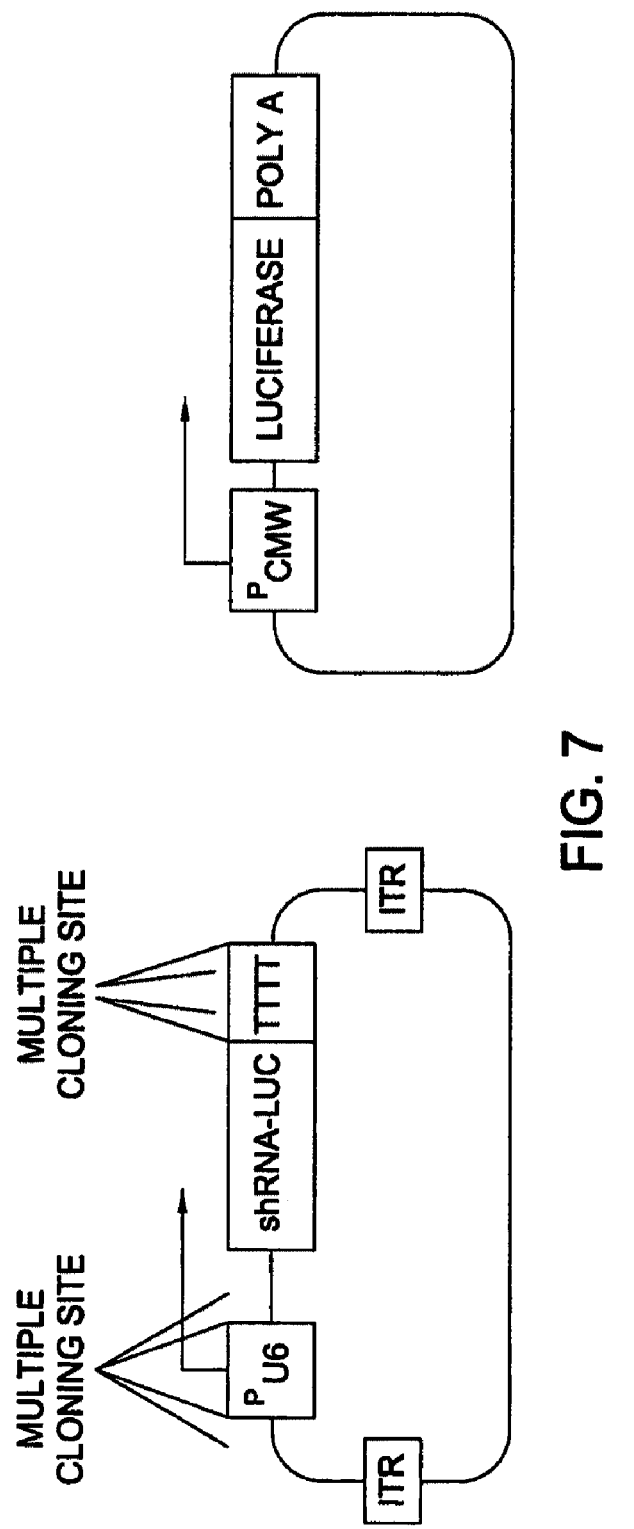
FIG. 7 is a schematic of a representative promoter testing construct and a reporter construct.

Initially, the assessment of relative promoter strength of the pol III-specific sequences is conducted in vectors containing the single, individual promoters (shown in FIG. 7). Each promoter construct drives expression of a shRNA that has demonstrated functional inhibition of luciferase activity (Elbashir, et al. *Nature*. 411: 494-498 (2001a)). Since there is a wealth of data demonstrating the successful utilization of the U6 promoter for the expression of shRNA, it is used as the standard for assessing the relative strength of other promoters. The majority of the promoters that are tested are quite short, most in the range of 200-300 nucleotides in length. Long, overlapping oligonucleotides are used to assemble the promoters and terminators de novo and are then cloned into multiple cloning sites that flank the shRNA. The promoter is paired with the termination signal that occurs naturally downstream of the gene from which the promoter is taken.

The relative strength of each promoter is assessed in vitro by the decrease in activity of a co-transfected commercially available luciferase reporter, pGL3Control (shown in FIG. 7) or pRLSV40 (Promega, Madison, Wis.). The test and reporter constructs are transfected into permissive cells utilizing standard techniques. Controls consist of a test promoter construct in which the functional shRNA against luciferase is replaced by an unrelated shRNA sequence. A third construct encoding for the secreted protein human α1-antitrypsin (hAAT) is co-transfected into the cells in order to assess for variations in transfection efficiencies. For assessing inhibitory activity of the shRNA, luciferase activity is measured utilizing standard commercial kits (Promega, Madison, Wis.). The shRNA-mediated decrease in luciferase expression, normalized to hAAT levels, is an indirect measurement of promoter strength. Alternatively or in addition, quantitative real time PCR analysis (Q-PCR) on luciferase RNA levels is performed on RNA that is harvested and purified from parallel experimental plates.

Once appropriate promoter and terminator pairs are identified, the final triple promoter RNAi expression cassette is designed. Several designs of the final vector are tested, including having all three promoters in a tandem array or arranged in clockwise and counterclockwise configurations (i.e., transcribed from the top and the bottom strand of the cassette DNA) or any variation thereof. Three such configurations are shown in FIGS. 3A, 3B and 3C.

The configurations shown in FIGS. 3B and 3C were transfected into cells and tested for inhibitory activity utilizing luciferase activity assays. Two or more promoters driving distinct RNAi species may result in an additive or synergistic inhibitory effect, thus, in order to assess the functionality and relative strength of each of the promoters within the context of the triple promoter expression construct, variants of the expression cassettes was generated as detailed in Table 4. Utilizing these species, the inhibitory effect of the shRNA driven from each promoter within the triple expression construct was measured by luciferase assays. Alternatively, Q-PCR is used to assess relative levels of transcript driven by each promoter. Although the self-complementary nature of hairpin-RNA generally would prevent the direct Q-PCR measurement of these RNA transcripts, three different non-hairpin transcripts of approximately the same size can be substituted into the vectors in place of the shRNA using viral multiple-promoter RNAi expression constructs with cassettes such as those shown in FIGS. 3D and 3E may be used.

The following RNA Pol III Class 3 promoters: U6-1, U6-8, U6-9, H1 Long, Human Y4, Human Y5, were selected, synthesized and cloned into either a single or multiple promoter construct. The luciferase specific shRNA was then cloned downstream of the single promoter construct or downstream of one of the promoters in the triple promoter construct (Table 4).

72 hours after transfection, the media was aspirated and the cells were lysed and measured for luciferase expression according to the manufacturer's dual luciferase protocol (Promega, Madison, Wis.). Percent of inhibition was calculated based on normalized luciferase relative light units (RLUs) versus mock-treated cells (the negative control). An unrelated RNAi agent was used as the mock/negative control in each experiment. Normalization of luciferase RLUs for transfection efficiency was made based on expression of Renilla luciferase expressed from pRL-SV40 plasmid co-transfected with the target plasmids.

All promoters were shown to be similarly active in both constructs of FIG. 3C type in Huh 7 cells (17A), and constructs of FIG. 3B type in 293 cells (17B). It can be seen that the inhibitory properties are similar for shRNA in single and multiple promoter contexts. The data showed that inhibition of the shRNA is comparable in a triple promoter context and in both Huh? and 293 cells.

TABLE 4

Promoter/shRNA inserts in constructs of the type shown in FIG. 3B and 3C used for assessing relative inhibitory contribution of each expression cassette

| | Promoter/shRNA | | |
|---|---|---|---|
| Construct | A<br>U6-1 | B<br>U6-8 | C<br>U6-9 |
| Construct I | shRNA-LUC | Empty | empty |
| Construct II | empty | shRNA-LUC | empty |
| Construct III | empty | Empty | shRNA-LUC |

Figure 20:
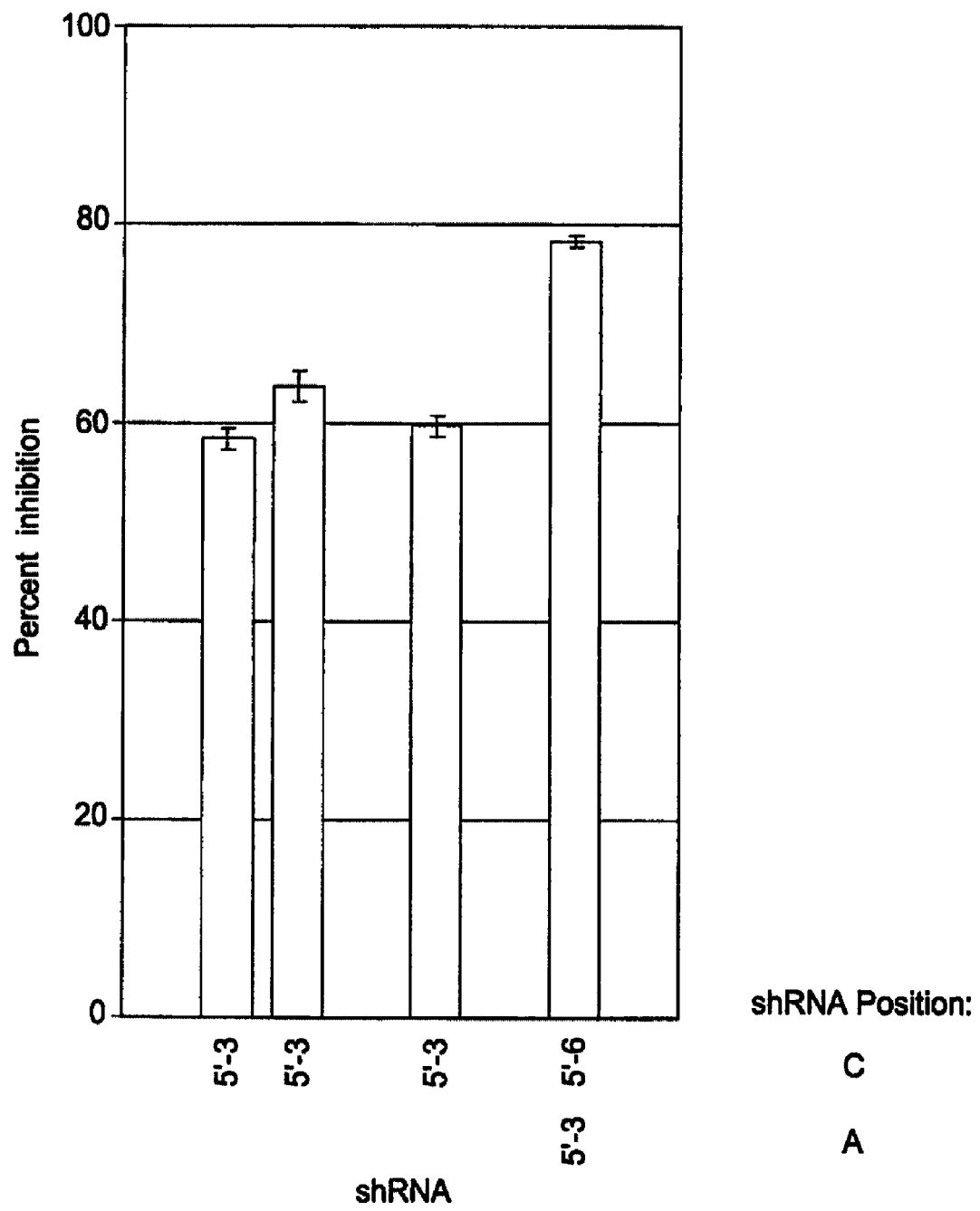
FIG. 20 shows the percent inhibition of luciferase signal from a luciferase-HCV reporter plasmid after co-transfection with plasmids comprising promoter/shRNA cassettes containing one or two active promoters.

Plasmids comprising the promoter/shRNA/terminator cassettes of the type shown in FIG. 3B were used to assess the relative inhibitory contribution of shRNA agents expressed from multiple promoter expression cassettes. Plasmids comprising shRNA constructs targeting different regions of the HCV genome are placed operably under the control of different promoters. Table 5 shows which shRNA are under the control of the separate promoters including shRNA agents under control of the promoter at position B that was inactive. Luciferase-HCV fusion plasmid #16 containing the HCV sequence from regions 5'-3 through 5'-linked to the luciferase gene was co-transfected into Huh7 cells along with multiple promoter constructs. FIG. 20 shows the increased inhibition of luciferase when co-transfected with a multiple promoter/ double shRNA expression construct as compared to a construct comprising a single shRNA linked to a single promoter.

TABLE 5

Promoter/shRNA inserts in constructs of the type shown in FIG. 3B used for assessing relative inhibitory contribution of an individual and dual promoters in a multiple promoter expression cassette.

| | Promoter/shRNA | | |
|---|---|---|---|
| Construct | A<br>U6-9 | B<br>inactive | C<br>U6-8 |
| Construct I | 5-'3 | 5'-1 | empty |
| Construct II | 5-'3 | C-12 | empty |
| Construct III | 5-'3 | 5'-8 | empty |
| Construct IV | 5-'3 | 5'-8 | 5'-6 |

Example 4B

Testing of shRNA Triple Promoter Constructs In Vitro

Figure 21:
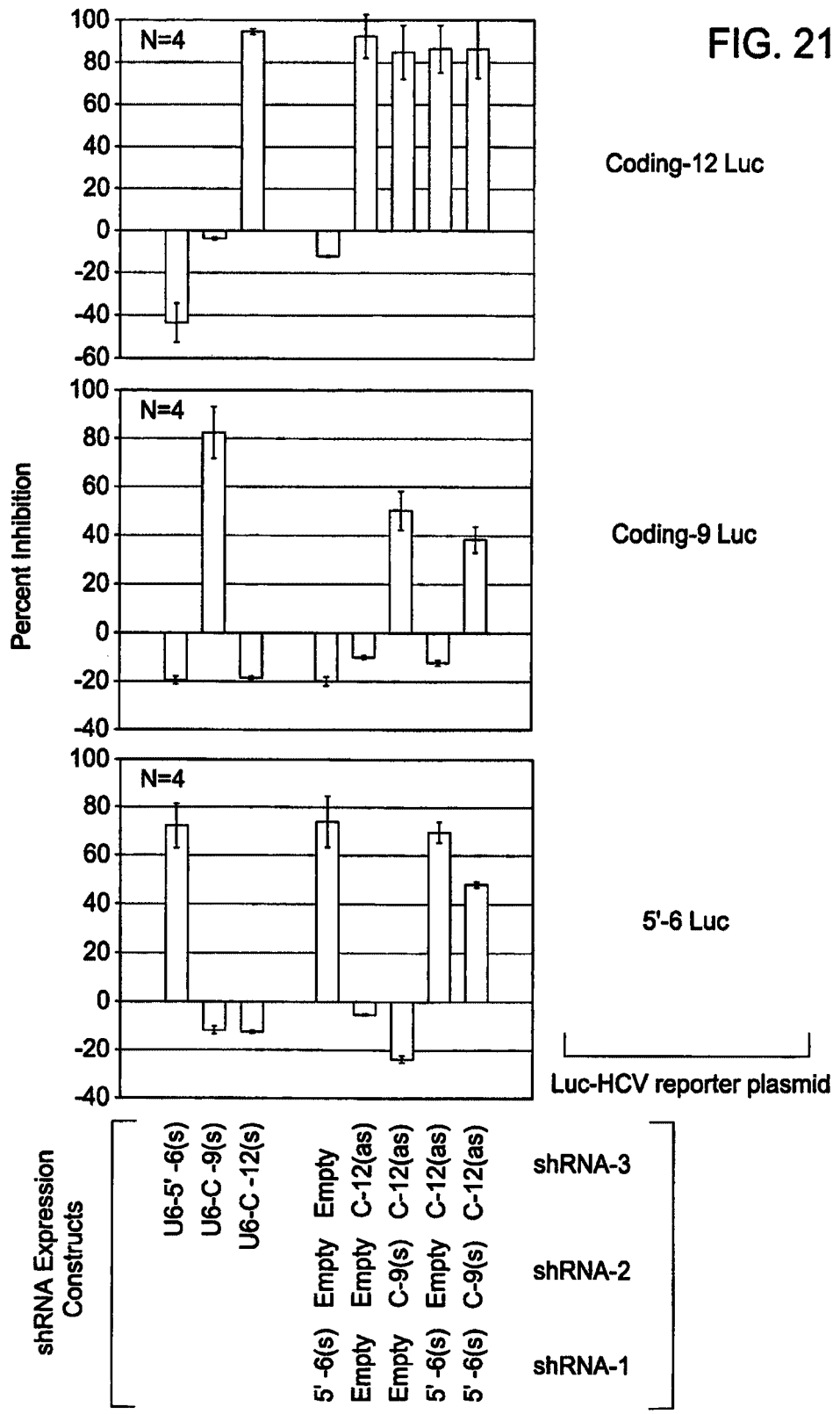
FIG. 21 shows the percent inhibition of luciferase signal from a luciferase-HCV reporter plasmid containing coding region C12 (top), coding region C-9 (middle), or 5'6 region (bottom) after co-transfection with plasmids comprising one, two or three active promoter/shRNA cassettes.

Triple promoter cassettes of the type shown in FIG. 3C were generated with the following promoters; U6-9 in position A, U6-1 in position B, and U6-8 in position C. The promoters drove transcription of shRNA sequences targeting various positions in the HCV genome or were followed by stretches of T's in the 'empty' configuration to prevent promoter read-through. Single promoter/shRNA constructs used as controls were constructed using the U6-1 promoter. The single or triple promoter constructs were co-transfected with luciferase-HCV reporter plasmids that contained different HCV target regions. FIG. 21 shows the results of luciferase inhibition after co-transfection with single or multiple promoter constructs that targeted different regions in the HCV genome and one of three luciferase-HCV fusion plasmids containing sequence from target regions in the HCV genome. Luciferase activity was measured 72 hours after co-transfection into Huh7 cells. It can be seen in the top graph in FIG. 21 that shRNA specific for the C-12 region of HCV shows the appropriate inhibitory activity to luciferase reporter plasmid containing the coding region C-12 of HCV. No non-specific inhibition is observed when shRNA specific for other regions of HCV are expressed either singly or as part of a multiple promoter cassette of this invention Similar results can be seen in the middle graph where the Luciferase-HCV reporter plasmid contains sequence from the coding region C-9 of HCV. In this case, shRNA specific to the C-9 region expressed either from a single promoter or triple promoter cassette had the strongest inhibitory activity of the shRNA agents tested. The bottom graph shows the luciferase inhibition resulting from co-transfection with single or triple promoter constructs and reporter plasmids containing the 5'6 region of HCV. It can be seen that the strongest inhibition results from constructs containing shRNA specific for the 5'6 target in either a single or multiple promoter construct. Triple promoter constructs of this invention work to effectively suppress specific gene targets.

Example 5

Testing of shRNA Triple Promoter Constructs Agents In Vivo

In vivo evaluation of multiple promoter constructs of this invention were assessed by co-transfection of mouse liver with the multiple promoter/shRNA plasmid DNA of the type shown in FIG. 3C and the appropriate firefly luciferase-HCV fusion reporter plasmid using the hydrodynamic tail vein injection procedure. The multiple promoter/shRNA plasmid used here controlled the expression of shRNA species that targeted the coding 9, coding 12 and the 5'8 position of HCV. Negative control mice were injected with the reporter construct and an irrelevant shRNA. In addition, mice were injected with plasmids expressing the renilla luciferase protein. This protein was used to normalize the transfection efficiency of mouse liver. Forty eight hours after injection, the animals were sacrificed, and the livers were harvested. Liver lysates were assayed for firefly luciferase activity and renilla luciferase activity using a Promega luciferase kit. Levels of inhibition induced by the shRNA expression from the hairpin constructs are assessed relative to the negative control. The results shown in Table 6 show that triple promoter constructs of this invention effectively inhibit reporter signal in vivo.

ing the AAV triple promoter expression vector and packaging components, remain unchanged. The model system for the hepatitis B virus (HBV) is utilized. Selection of shRNA sequences to be included in the triple promoter AAV expression construct to target HBV are chosen based on the efficacy of shRNA sequences published to date (McCaffrey, et al. *Nature Biotech.* 21(6): 639-644 (2003); Ying, et al. *Biochem. Biophys. Res. Commun.* 309(2): 482-484 (2003); Klein, et al. *Gastroent.* 125(1): 9-18 (2003); and Shlomai, et al. *Hepatology.* 37(4): 764-70 (2003)). The appropriate AAV expression construct with the triple promoter driving three HBV-specific shRNAs is then packaged into viral particles according to the methods described herein.

The mice are first injected by hydrodynamic transfection procedures with the expression plasmids bearing the

TABLE 6

Percent inhibition of firefly luciferase signal by triple promoter/shRNA plasmid

| Group # | n | Plasmid expressing shRNA (5 μg/mouse) | Reporter plasmid (12 μg/mouse) | Firefly Luciferase RLU (normalized to *Renilla*) | % Inhibition by Triple shRNA Compared to non-specific shRNA Control |
|---|---|---|---|---|---|
| 21 | 5 | Triple promoter/shRNA (5'8as, C-9s, C-12as) | C-9 (pBen71) | 0.05 | 98% |
| 23 | 5 | Single non-specific 5'-3 (non-specific shRNA) | C-9 (pBen71) | 3.20 | n/a |
| 25 | 5 | Triple promoter/shRNA (5'8as, C-9s, C-12as) | C-11/12 (pBen73) | 1.00 | 93% |
| 27 | 5 | Single non-specific 5'-3 (non-specific shRNA) | C-11/12 (pBen73) | 15.10 | n/a |

Infectious AAV particles containing vectors that express the shRNA targeted against HCV sequences are delivered to normal mice either by tail vein or hepatic portal vein injection. Infectious AAV particles expressing three unrelated shRNAs serve as the negative control. Initially, a fairly high dose of virus, e.g. $2\times10^{12}$ vector genomes, is used, though subsequent experiments are performed to establish dose-response curves. An appropriate firefly luciferase-HCV fusion reporter plasmid is injected at various times using the hydrodynamic tail vein injection procedure. 48-72 hours after injection of the reporter plasmid, the mice are sacrificed, the livers harvested and samples of serum collected. Firefly luciferase activity is used as a benchmark to assess efficacy of the AAV delivered shRNA. In addition, monitoring the serum levels of hAAT or liver levels of renilla luciferase are used to determine transfection efficiency between animals. Serum levels of the liver enzymes alanine aminotransferase, aspartate aminotransferase, and tumor necrosis factor alpha are measured to ensure general hepatic toxicity is not induced by the treatment.

Example 6

Testing AAV-Delivery of shRNA Against an In Vivo Replicating HBV Model System

There is no ideal small animal model for testing the efficacy of AAV-delivered shRNA expression constructs against HCV. However, testing the AAV expression RNAi construct in an alternate model system may be used to assess the extent of inhibition of viral replication in the liver. Although the sequence composition of the delivered shRNA is necessarily different in such a model, the remainder of the system, includsequences of the HBV genome and are allowed to establish HBV replication. In order to assess transfection efficiency, a plasmid encoding for hAAT is added into the mixture for co-injection. Initial indications of HBV activity is assessed by the appearance of Hepatitis B Virus surface antigen (HBsAg) and the HBV core antigen (HBcAg) in the serum of the treated animals by ELISA assays collected by retro-orbital plexus bleed.

Following establishment of HBV replication in the mouse livers, the AAV viral particles packaging the triple promoter constructs encoding HBV shRNAs are introduced into the mouse using tail vein injection or hepatic portal vein injection. AAV viral particles bearing an AAV expression construct encoding three HBV-unrelated shRNAs are utilized as a negative control. At the termination of the experiment, serum samples are monitored for down regulation of the quantities of HBsAg and HBcAg proteins. Alternatively or in addition, liver tissues are assessed for the relative levels of HBV RNA by Q-PCR. Systemic liver toxicity is evaluated by monitoring serum for alanine aminotransferase, aspartate aminotransferase, and tumor necrosis factor alpha by ELISA.

Figure 10:
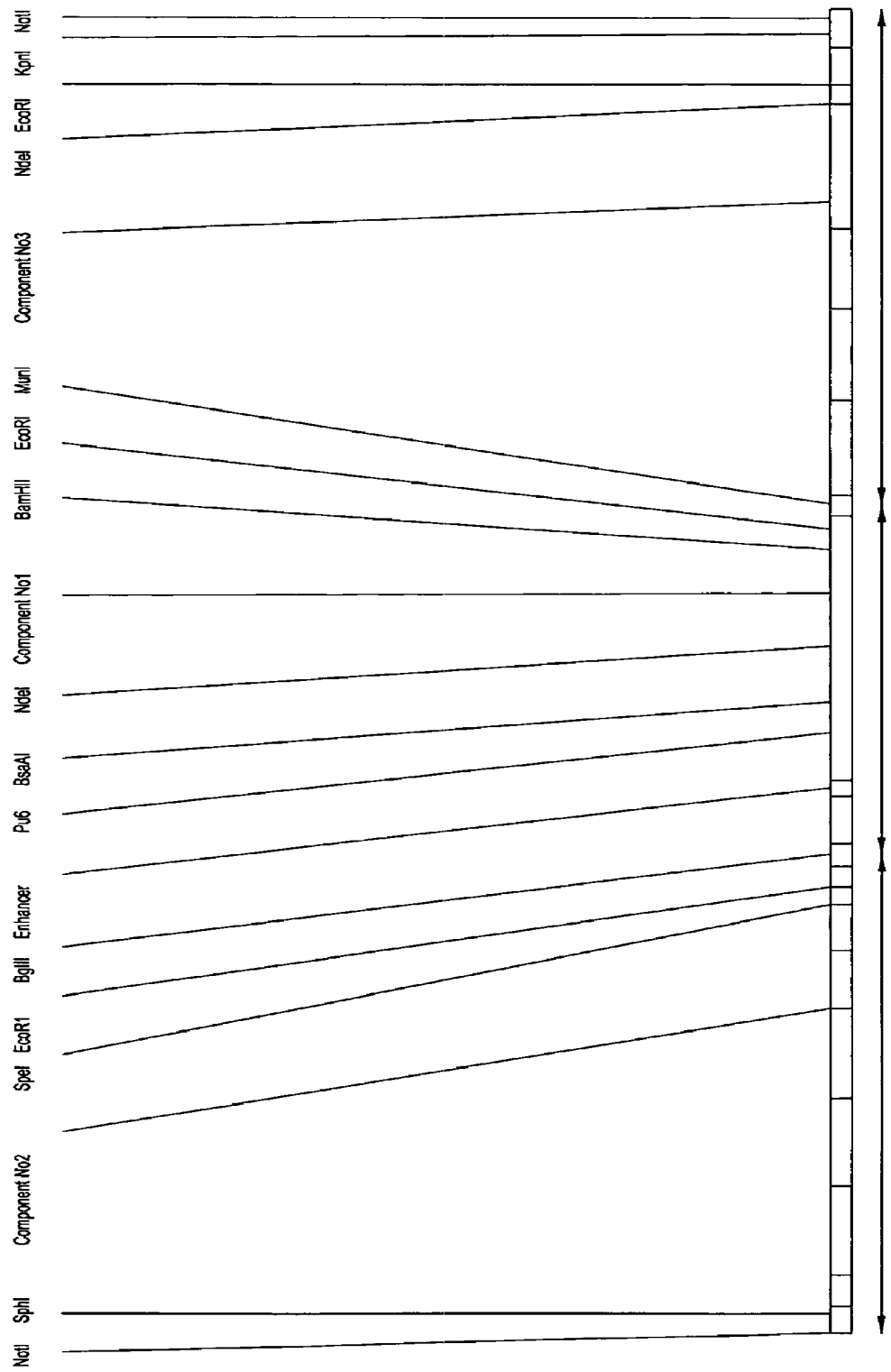
FIG. 10 is a graphic illustration of one embodiment of a triple promoter cassette showing unique restriction sites useful for modular assembly of various RNAi agents, promoter elements and terminator elements.

FIG. 10 is a graphic illustration of one embodiment of a precursor triple promoter cassette showing unique restriction sites useful for inserting or removing RNAi species or terminator elements or for switching out the U6-9, pU6 or U6-8 promoters shown. In addition, arrows show the direction of transcription of each of the three promoter/RNAi/terminator components. FIGS. 11A and 11B/11C show the nucleotide sequence (SEQ ID NO 31 and 32, respectively) of two embodiments of the precursor promoter cassettes of this invention. FIG. 10, shows the locations of the U6-9, pU6 or U6-8 promoters, as well as the restriction sites of a precursor promoter cassette of this invention.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material or process to the objective, spirit and scope of the present invention. All such modifications are intended to be within the scope of the invention.

All references cited herein are to aid in the understanding of the invention, and are incorporated in their entireties for all purposes without limitation.

What is claimed is:

1. A genetic construct comprising a multi-promoter expression cassette comprising at least three promoter/RNAi/terminator components wherein each promoter/RNAi/terminator component comprises a promoter element, a terminator element and a sequence encoding an RNAi species operably linked to the promoter element and the terminator element, wherein at least one of the RNAi species is encoded by SEQ ID NO: 22.

2. The genetic construct of claim 1, wherein the genetic construct further comprises elements necessary for packaging of the construct into infectious virus particles.

3. The genetic construct of claim 1, wherein the sequence of two of the terminator elements in each promoter/RNAi/terminator component is different from one another.

4. The genetic construct of claim 1, wherein the sequence of two of the promoter elements in each promoter/RNAi/terminator component is different from one another.

5. The genetic construct of claim 1, wherein the three or more RNAi species target a nucleic acid sequence having sequence single nucleotide polymorphisms (SNPs) between variants, and each of the RNAi species can target one or more subsets of variants.

6. The genetic construct of claim 1, wherein the three or more RNAi species target nucleic acid sequences that undergo rapid mutation.

7. The genetic construct of claim 1, wherein the sequence of the RNAi species targets one or more variants of a nucleic acid sequence.

8. The genetic construct of claim 1 wherein the RNAi species are based upon the sequence of a target nucleic acid and additionally are based upon sequences having point mutations that arise to resist RNAi treatment.

9. The genetic construct of claim 1, wherein at least one of the RNAi species is encoded by SEQ ID NO:6 or SEQ ID NO: 19.

10. The genetic construct of claim 1, wherein the RNAi species are encoded by SEQ ID NOS: 6, 19 and 22.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 1
gctgtgagga actactgtct                                               20

<210> SEQ ID NO 2
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 2
gtctagccat ggcgttagt                                                19

<210> SEQ ID NO 3
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 3
ggagagccat agtggtctg                                                19

<210> SEQ ID NO 4
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 4
gcggaaccgg tgagtacac                                                19

<210> SEQ ID NO 5
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 5
gtctgcggaa ccggtgagta                                               20

<210> SEQ ID NO 6
<211> LENGTH: 20
<212> TYPE: DNA
<213> ORGANISM: Artificial sequence
<220> FEATURE:
<223> OTHER INFORMATION: Target sequence for RNAi of Hepatitis C virus
```

```
<400> SEQUENCE: 6
gcgaaaggcc ttgtggtact                                              20

<210> SEQ ID NO 7
<211> LENGTH: 19
<212> TYPE: DNA
<213> ORGANISM: Artificial sequence
<220> FEATURE:
<223> OTHER INFORMATION: Target sequence for RNAi of Hepatitus C Virus

<400> SEQUENCE: 7
gatagggtgc ttgcgagtg                                               19

<210> SEQ ID NO 8
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 8
gaggtctcgt agaccgtgca                                              20

<210> SEQ ID NO 9
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 9
gcttgtggta ctgcctgata                                              20

<210> SEQ ID NO 10
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 10
gctgcctgat agggtgcttg                                              20

<210> SEQ ID NO 11
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 11
agatcgttgg tggagttta                                               19

<210> SEQ ID NO 12
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 12
gttgggtaag gtcatcgata                                              20

<210> SEQ ID NO 13
<211> LENGTH: 20
<212> TYPE: DNA
```

<213> ORGANISM: Artificial sequence
<220> FEATURE:
<223> OTHER INFORMATION: Target sequence for RNAi of Hepatitis C virus

<400> SEQUENCE: 13
gccgacctca tggggtacat                                              20

<210> SEQ ID NO 14
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 14
ggttgctctt tctctatct                                               19

<210> SEQ ID NO 15
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 15
gggatatgat gatgaactg                                               19

<210> SEQ ID NO 16
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 16
ggatgaaccg gctaatagc                                               19

<210> SEQ ID NO 17
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 17
ggagatgggc ggcaacatc                                               19

<210> SEQ ID NO 18
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 18
gtcttcacgg aggctatga                                               19

<210> SEQ ID NO 19
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 19
gtcaactcct ggctaggcaa                                              20

```
<210> SEQ ID NO 20
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 20
gtccacagtt actctccagg                                                   20

<210> SEQ ID NO 21
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 21
gcctcttcaa ctgggcagta                                                   20

<210> SEQ ID NO 22
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 22
agcttaaact cactccaat                                                    19

<210> SEQ ID NO 23
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 23
gctccatctt agccctagt                                                    19

<210> SEQ ID NO 24
<211> LENGTH: 20
<212> TYPE: DNA
<213> ORGANISM: Artificial sequence
<220> FEATURE:
<223> OTHER INFORMATION: Target sequence for RNAi of Hepatitis C virus

<400> SEQUENCE: 24
gtccatctta gccctagtca                                                   20

<210> SEQ ID NO 25
<211> LENGTH: 19
<212> TYPE: DNA
<213> ORGANISM: Artificial sequence
<220> FEATURE:
<223> OTHER INFORMATION: Target sequence for RNAi of Hepatitis C virus

<400> SEQUENCE: 25
gtcacggcta gctgtgaaa                                                    19

<210> SEQ ID NO 26
<211> LENGTH: 19
<212> TYPE: DNA
<213> ORGANISM: Artificial
<220> FEATURE:
<223> OTHER INFORMATION: Target sequence for RNAi of Hepatitis C virus
```

```
<400> SEQUENCE: 26
acggctagct gtgaaaggt                                                    19

<210> S

```
agaaagtaat aatttcttgg gtagtttgca gttttaaaat tatgttttaa aatggactat      600
catatgctta ccgtaacttg aaagtatttc gatttcttgg ctttatatat cttgtggaaa      660
ggacgaggat ccggttattt ttttcaattg atctagaaaa aaaaaagcta gtggtaccgg      720
tcctacgcgg ggccctttac ccagggtgcc ccgggcgctc atttgcatgt cccacccaac      780
aggtaaacct gacaggtcat cgcggccagg tacgacctgg cggtcagagc accaaacata      840
cgagccttgt gatgagttcc gttgcatgaa attctcccaa aggctccaag atggacagga      900
aagggcgcgg ttcggtcacc gtaagtagaa taggtgaaag actcccgtgc cttataaggc      960
ctgtgggtga cttcttgcta gcgaccttac gtgttcatgg aattctgtac cgtatatagc     1020
atgactgcgg ccgccaattc atctatgtcg ggtgcggaga agaggtaat  gaaatggcat     1080 tatgggtatt atgggtctgc attaatgaat cggccaacgc gcggggagag gcggtttgcg     1140
tattgggcgc tctt                                                       1154

<210> SEQ ID NO 32
<211> LENGTH: 1971
<212> TYPE: DNA
<213> ORGANISM: Artificial sequence
<220> FEATURE:
<223> OTHER INFORMATION: Multiple expression cassette for RNAi

<400> SEQUENCE: 32
ataaacaaat aggggttccg cgcacatttc cccgaaaagt gccacctgac gtaactataa       60
cggtcctaag gtagcgaaag ctcagatccg cggccgcgta gtacgatgac tagcatgcag      120
ggcggtgcgg ctcaggctct gccccgcctc cggggctatt tgcatacgac catttccagt      180
aattcccagc agccaccgta gctatatttg gtagaacaac gagcactttc tcaactccag      240
tcaataacta cgttagttgc attacacatt gggctaatat aaatagaggt taaatctcta      300
ggtcatttaa gagaagtcgg cctatgtgta cagacatttg ttccaggggc tttaaatagc      360
tggtggtgga actcaactag tgtagatttt tttctgcagg catagcagag atctgttcgg      420
ctttacgtca cgcgagggcg gcagggagga cggaatggcg gggtttgggg tgggtccctc      480 ctcggggag  ccctgggaaa agaggactgc gtgtgggaag agaaggtgga aatggcgttt      540
tggttgacat gtgccgcctg cgagcgtgct gcggggaggg gccgagggca gattcgggaa      600
tgatggcgcg gggtggggc  gtgggggctt tctcggagga ggcccttccc tggaagtttg      660
gggtgcgatg gtgaggttct cggggcacct ctggagggc  ctcggcacgg aaagcgacca      720
cctgggaggg cgtgtgggga ccaggttttg cctttagttt tgcacacact gtagttcatc      780
tttatggaga tgctcatggc ctcattgaag ccccacggat ctgggcagga agagggccta      840
tttcccatga ttccttcata tttgcatata cgatacaagg ctgttagaga gataattaga      900
attaatttga ctgtaaacac aaagatatta gtacaaaata cgtgacgtag aaagtaataa      960
tttcttgggt agtttgcagt tttaaaatta tgttttaaaa tggactatca tatgcttacc     1020
gtaacttgaa agtatttcga tttcttggct ttatatatct tgtggaaagg acgaggatcc     1080
ggttattttt tcaattgta cagctctggt agcggtaacc atgcgtattt gacacacgaa     1140
ggaactaggg aaaaggcatt aggtcatttc aagccgaaat tcacatgtgc tagaatccag     1200
attccatgct gaccgatgcc ccaggatata gaaaatgaga atctggtcct taccttcaag     1260
aacattctta accgtaatca gcctctggta tcttagctcc accctcactg gtttttcttt     1320
gtttgttgaa ccggccaagc tgctggcctc cctcctcaac cgttctgatc atgcttgcta     1380
aaatagtcaa aaccccggcc agttaaatat gctttagcct gctttattat gattattttt     1440
```

-continued

```
gttgttttgg caatgacctg gctacctgtt gtttctccca ctaaaacttt ttaagggcag   1500
ggaattgatc tagaaaaaaa aaagctagtg gtaccggtcc tacgcggggc cctttaccca   1560
gggtgccccg ggcgctcatt tgcatgtccc acccaacagg taaacctgac aggtcatcgc   1620
ggccaggtac gacctggcgg tcagagcacc aaacatacga gccttgtgat gagttccgtt   1680
gcatgaaatt ctcccaaagg ctccaagatg gacaggaaag ggcgcggttc ggtcaccgta   1740
agtagaatag gtgaaagact cccgtgcctt ataaggcctg tgggtgactt cttgctagcg   1800
accttacgtg ttcatggaat tctgtaccgt atatagcatg actgcggccg ccaattcatc   1860
tatgtcgggt gcggagaaag aggtaatgaa atggcattat gggtattatg ggtctgcatt   1920
aatgaatcgg ccaacgcgcg gggagaggcg gtttgcgtat tgggcgctct t            1971
```